United States Patent
Leong et al.

(10) Patent No.: US 6,797,704 B2
(45) Date of Patent: Sep. 28, 2004

(54) SYSTEMIC DELIVERY OF COMPOUNDS THROUGH NON-INVASIVE BLADDER ADMINISTRATION

(75) Inventors: Kam W. Leong, Ellicott City, MD (US); Michael F. Haller, Baltimore, MD (US); Bernard A. Malavaud, Toulouse (FR); Catherine S. Le Visage, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/972,725

(22) Filed: Oct. 5, 2001

(65) Prior Publication Data

US 2002/0172717 A1 Nov. 21, 2002

Related U.S. Application Data

(60) Provisional application No. 60/238,505, filed on Oct. 6, 2000.

(51) Int. Cl.[7] .............................................. A61K 48/00
(52) U.S. Cl. ........................ 514/44; 424/468; 424/482; 424/486; 514/2
(58) Field of Search ................................ 424/486, 468, 424/482; 435/320.1, 455; 514/44, 2

(56) References Cited

FOREIGN PATENT DOCUMENTS

| EP | 0333523 | 9/1989 |
|---|---|---|
| WO | WO 99/65531 | 12/1999 |
| WO | WO 00/41678 | 7/2000 |
| WO | WO 01/68052 | 9/2001 |

OTHER PUBLICATIONS

Anderson, Nature, vol. 392, pp. 25–30, Apr. 1998.*
Verma, Nature, vol. 389, pp. 239–242, 1997.*
McCluskie et al. (Molecular Medicine, 5, pp. 287–300, 1999).*
Muzaffer, International Journal of Pharmaceutics, 235, 1, 2, 51–9, 2002.*
McKenzie, Immunologic Res, 24,3:225–244, 2001.*

* cited by examiner

Primary Examiner—Dave Trong Nguyen
(74) Attorney, Agent, or Firm—Peter F. Corless; John B. Alexander; Edwards & Angell LLP

(57) ABSTRACT

The present invention features methods of administering a therapeutic agent to a patient's lymph nodes by instillation of microparticles or nanoparticles comprising a biocompatible polymer and the therapeutic agent into the patient's bladder. The invention also features methods of modulating a patient's immune response and methods of systemic delivery of a therapeutic agent systemically using the administration methods of the invention.

32 Claims, 9 Drawing Sheets

SYSTEMIC DELIVERY OF COMPOUNDS THROUGH NON-INVASIVE BLADDER ADMINISTRATION

This application claims the benefit of U.S. Provisional Application Serial No. 60/238,505 filed Oct. 6, 2000, the teachings of which are incorporated herein by reference.

GOVERNMENT SUPPORT

This work described herein was supported by a grant from the National Institute of Health. Therefore, the U.S. Government may have certain rights in the invention.

FIELD OF THE INVENTION

The present invention provides methods for the delivery of a therapeutic agent to lymph nodes or other targeted tissues via the bladder. In particular, the methods of the invention provide the use of microparticles or nanoparticles comprising a biocompatible polymer and the therapeutic agent where the microparticles or nanoparticles are non-invasively instilled into the bladder and subsequently localized to the lymph node whereupon the therapeutic agent is released from the polymer matrix. The present invention further relates to methods of modulating immune response and methods of systemically administering a therapeutic using bladder delivery of microparticles.

BACKGROUND OF THE INVENTION

Administration via the bladder has been used as a route of delivery for local treatments of bladder cancer, but no examples have been disclosed of molecular uptake from the bladder where the molecule was transported to another tissues. For example, one study that used replication-deficient adenovirus to transfect bladder cells with the beta-galactosidase and p53 genese found no evidence of cellular transfection in the liver, lung, or heart of treated animals (Werthman, P. E., K. E. Drazan, J. T. Rosenthal, R. Khalili, and A. Shaked, *Adenoviral-p53 gene transfer to orthotopic and peritoneal murine bladder cancer.* Journal of Urology, 1996. 155(2): p. 753–756). It has also been shown that when $^{125}$I-interferon-α protein encapsulated in phosphtidylcholine/phosphatidyserine liposomes was instilled into C57BL/6 mice, systemic absorption was negligible, as evidenced by examination of amount of radiation in the kidney, spleen, liver, and lungs (Frangos, D. N., J. J. Killion, D. Fan, R. Fishbeck, A. C. von Eschenbach, and I. J. Fidler, *The development of liposomes containing interferon alpha for the intravesical therapy of human superficial bladder cancer.* Journal of Urology, 1990. 143(6): p. 1252–6). Finally, systemic absorption of doxorubicin following intravesical administration is minimal (Jacobi, G. H. and K. H. Kurth, *Studies on the intravesical action of topically administered G3H—doxorubicin hydrochloride in men: plasma uptake and tumor penetration.* J Urol, 1980. 124(1) 34–7). Thus, it has been demonstrated in these studies that drugs, proteins, and genes remain localized to the bladder following bladder instillation.

There are currently many different routes that can be used to administer drugs, proteins, and genes systemically. Each has unique advantages and disadvantages, and each is useful in certain situations; there is no one "best" method for delivering molecules systemically. For example, intravenous injection of the compound allows 100% of the dose to be transferred to the patient and the compound is rapidly carried throughout the body through the bloodstream. However, injection with needles carries the possibility of infection, as one of the body's primary barriers to infection is breached; this is especially a problem when the needle is not sterile. Furthermore, injections can be painful and most often must be performed by trained medical staff, which increases the cost of the procedure. Also, once the molecule is injected into the blood, serum proteins can rapidly bind to and inactivate it; many molecules thus have short serum half-lives.

Oral administration is promising in many cases, as the patient can self-administer the dose and the administered molecules can be delivered to specific areas of the digestive tract. For example, the gut-associated lymphoid tissue (GALT) is an inviting area of the gut for the administration of vaccines (Jones, D. H., J. C. Clegg, and G. H. Farrar, *Oral delivery of micro-encapsulated DNA vaccines.* Developments in Biological Standardization, 1998. 92: p. 149–55). Molecules delivered orally must pass through the acidic environment of the stomach, though, which often causes substantial degradation of the administered dose. Unprotected "naked" DNA, for instance, is totally inactivated in the stomach. Carriers such as chitosan and poly(lactic-co-glycolic acid) (PLGA) have been used to protect the molecular load from the hard environment of the stomach (Jones, D. H., J. C. Clegg, and G. H. Farrar, *Oral delivery of micro-encapsulated DNA vaccines.* Developments in Biological Standardization, 1998. 92: p. 149–55; Roy, K., H. Q. Mao, S. K. Huang, and K. W. Leong, *Oral gene delivery with chitosan—DNA nanoparticles generates immunologic protection in a murine model of peanut allergy.* Nature Medicine, 1999. 5(4): p. 387–91; Kofler, N., C. Ruedl, C. Rieser, G. Wick, and H. Wolf, *Oral immunization with poly-(D,L-lactide-co-glycolide) and poly-(L-lactic acid) microspheres containing pneumotropic bacterial antigens.* International Archives of Allergy & Immunology, 1997. 113(4): p. 424–31). Following passage through the stomach, the molecules must be taken up by various areas of the intestines, which is inefficient for many compounds (sources). Improvements in the uptake have been made in many cases. In one example, 0.5% of administered nanospheres were taken up, which was improved to 23% by the addition of lectin receptors to the nanospheres. After uptake by the gut, most molecules will travel to the liver and will be subjected to degradative enzymes in this first-pass hepatic metabolism. In most case, the majority of the administered dose is thus lost.

Advantages and disadvantages of a variety of application methods for systemic delivery of a therapeutic agent are tabulated in Table I. A number of application methods are known in the art and include intramuscular, oral, intravenous, intraperitoneal, subcutaneous, intranasal, pulmonary, transdermal, intradermal, buccal, sublingual, vaginal and rectal. Each common method of administration has disadvantages including low uptake of therapeutic agent, poor systematic absorption of the therapeutic agent, plasma protein bonding to the therapeutic agent, therapeutic agent degradation in the gastrointestinal tact or in the liver, difficult or painful administration procedures and the like. Other methods of delivery of a therapeutic agent are still needed which have therapeutic agent uptake and high systemic delivery.

In bladder instillation studies to date it has been demonstrated that instillation of molecules and particles do not lead to systemic uptake; the prior art teaches that bladder instillation of a therapeutic is only suitable for treatment for locally-occurring disorders such as bladder cancer. Molecules which have been instilled in the bladder including low molecular weight chemotherapeutic drugs like taxol, proteins such as interferon-α, viruses such as the adenovirus, and nonviral gene-containing liposomes are not transfected to other internal organs such as lung, spleen, kidney, liver or the like.

SUMMARY OF THE INVENTION

The present invention provides methods of administering a therapeutic agent to the lymph nodes, systemically delivering a therapeutic agent and modulating immune response by instilling microparticles or nanoparticles in the bladder. The methods of the invention use microparticles and nanoparticles which are taken up by the bladder, exit the bladder via lymphatics and are transported to the lymph nodes. Any therapeutic agent compatible with a polymer suitable for use in microspheres and nanospheres suitable for use in the methods of the invention may be administered to the lymph node or be distributed systemically by the methods of the invention. Preferred therapeutics include drugs, pro-drugs, proteins and genes.

The present invention provides microparticles and nanoparticles comprising a therapeutic agent and a biodegradable poly(phosphoester) that are taken up by the bladder tissue, are transported through lymphatic vessels, and are deposited in the lymph nodes within three hours of instillation. This transport occurs with high efficiency; more than 90% of the administered dose remains in the animal, which compares favorably with conventional oral administration, where often 10% or less of the administered dose is taken up. We have examined the mechanism of this transport and have shown that the particles are taken up inside vesicles in epithelial cells, which aids their transport through the epithelial layer to the draining lymphatics.

We have fabricated nanometer-sized spheres (nanospheres) which are taken up into the bladder wall following noninvasive bladder instillation. More than 90% of the instilled dose remains in the animal. After a short time inside the bladder wall, these nanospheres exit the bladder via the lymphatics and are transported to the lymph nodes. Drugs, proteins, and genes may be delivered from the nanospheres to the surrounding cells. Thus, the bladder represents a new route of administration to give a systemic response to the administered molecules.

In one aspect, the present invention provides a method of delivering a therapeutic agent to a patient's lymph node comprising
  providing a microparticle or nanoparticle composition comprising at least one biocompatible polymer and at least one therapeutic agent;
  instilling at least one microparticle or nanoparticle into a patient's bladder such that at least a portion of the instilled microparticle or nanoparticles are localized to the lymph nodes; and
  releasing at least a portion of the therapeutic agent from the microparticle into the lymph node.

The present invention also relates to methods for modulating immune response comprising the steps of:
  instilling at least one microparticle with one or more encapsulated therapeutic agents capable of modulating immune response to the bladder of a patient, transporting the microparticles to the lymph node and releasing the encapsulated therapeutic agent to modulate the immune response of the patient.

The present invention further provides a method for systemic delivery of a therapeutic agent to a patient, the method comprising the steps of:
  providing a microparticle or nanoparticle composition comprising at least one biocompatible instilling at least one microparticle comprising a therapeutic agent into a patient's bladder under conditions conducive to the transport of at least a portion of the microparticles across the epithelial layer of the bladder; and
  releasing at least a portion of the therapeutic agent from the microparticle such that the therapeutic agent is distributed systemically.

BRIEF DESCRIPTION OF THE DRAWINGS

For a fuller understanding of the present invention, reference is made to the following detailed description taken in conjunction with the accompanying figures wherein.

DETAILED DESCRIPTION OF THE INVENTION

Figure 1:
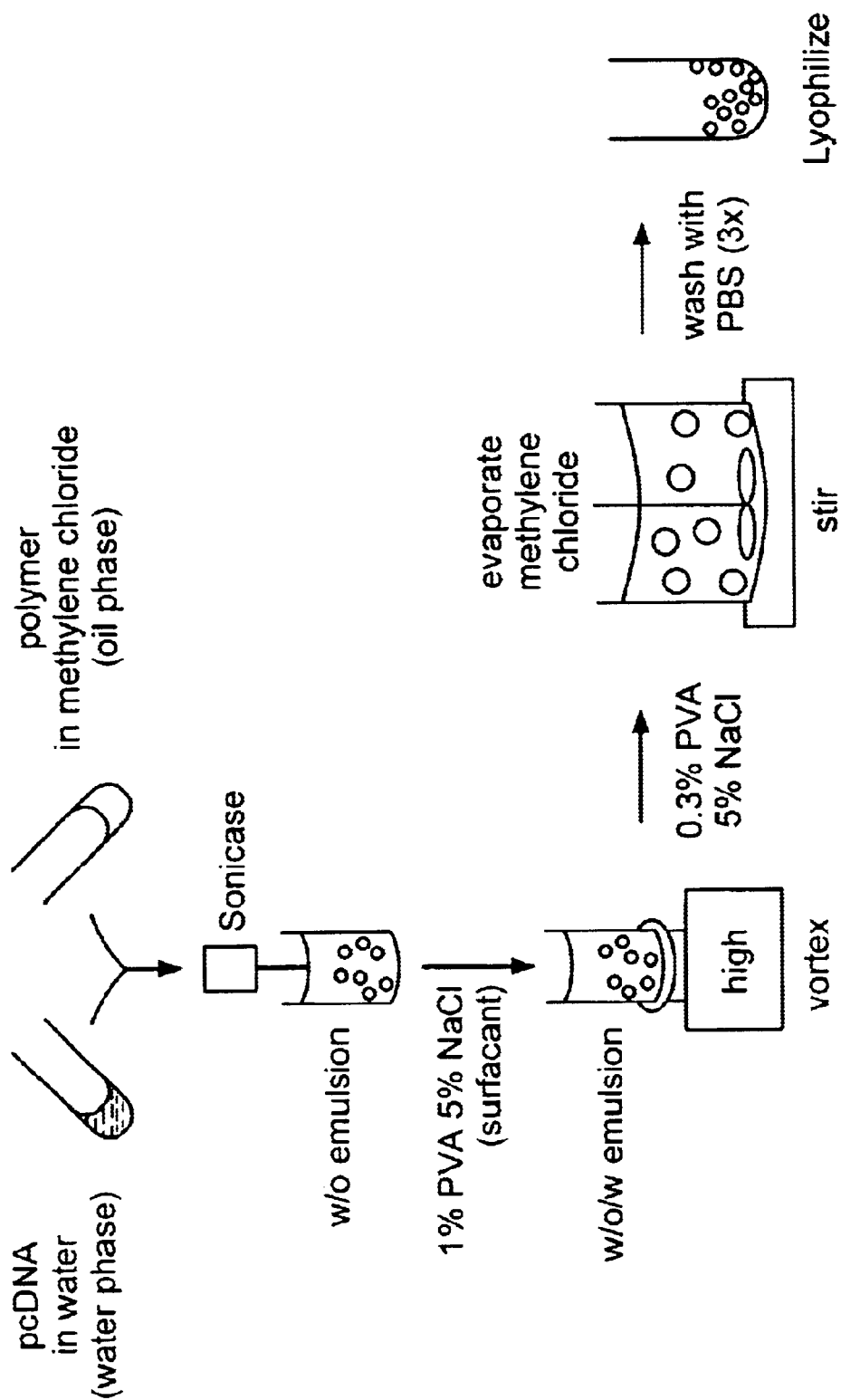
FIG. 1 is a schematic representation of the procedure for producing microspheres and nanospheres of the invention having DNA dispersed therein.

In one aspect, the present invention provides methods of delivering a therapeutic agent to a patient's lymph node comprising
  providing a microparticle or nanoparticle composition comprising at least one biocompatible polymer and at least one therapeutic agent;
  instilling at least one microparticle or nanoparticle into a patient's bladder such that at least a portion of the instilled microparticle or nanoparticles are localized to the lymph nodes; and releasing at least a portion of the therapeutic agent from the microparticle into the lymph node.

In preferred methods of deliverying a therapeutic agent to lymph nodes, the therapeutic agent delivered to the lymph node or a biologically active substance generated by delivery of a therapeutic agent to the lymph node from the microparticle into the lymph node is distributed systemically. Typically the therapeutic agent is selected from small molecule drugs, imaging agents, radioactive therapeutics, dyes, proteins, DNA and RNA. More preferably, the therapeutic agent is selected from the group consisting of DNA encoding vaccines, therapeutic agents, cytokines, immunoadjuvants, cancer therapeutic agents, proteins, and combinations thereof.

Other preferred therapeutic agents are substances that are capable of modulating the immune response of a patient. Preferred therapeutic agents capable of modulating an immune response include protein vaccines or DNA vaccines. More preferred therapeutic agents capable of modulating an immune response are DNA vaccines. In general, DNA vaccine include vaccines which comprise a DNA sequence encoding an antigen, DNA sequence encoding a cytokine or a combination of DNA sequence encoding an antigen and DNA sequence encoding a cytokine.

Preferred cytokine additives suitable for use in a DNA vaccine include cytokines selected from interleukins or interferons which can shift a patient's immune response toward either a $T_H1$ or $T_H2$ response. Preferred cytokines suitable for use in modulating an immune response include interleukin-12, interleukin-10, interleukin-5, interleukin-4 and interferon-gamma.

Polymeric microspheres and nanospheres suitable for use in the methods of the present invention to deliver a therapeutic agent are not particularly limited. Microspheres are a controlled-release device that has been used to encapsulate drugs, proteins, DNA and mixtures thereof. Typically polymers suitable for use in microspheres and nanospheres are biocompatible, biodegradable and may be formed into microspheres or nanospheres by single or double emulsion techniques which are known in the art. Preferred polymers include poly(lactic acid), poly(lactide), poly(lactic-co-glycolic acid) and copolymers of lactic acid and phosphate. More preferred polymers and microspheres include poly (phosphoester-co-lactic acid) copolymers recited in U.S. Pat. No. 6,166,173 and in copending U.S. patent application U.S. Ser. No. 09/803,358. Most preferred are copolymers of lactic acid, propylene oxide and ethyl phosphate and other related copolymers which are suitable for uptake of DNA, proteins or small biologically active substances. A particularly preferred polymer suitable for use in the present invention is P(DAPG-EOP), which is depicted below.

(propylene oxide). More preferred are microparticles or nanoparticles comprising at least one biocompatible polymer of the nanoparticle is a poly(phosphoester)-poly(D,L-lactide-co-ethylphosphate) copolymer.

Other preferred microparticles suitable for use in the methods of the invention comprise one or more biocompatible polymer having repeat units according to Formula I:

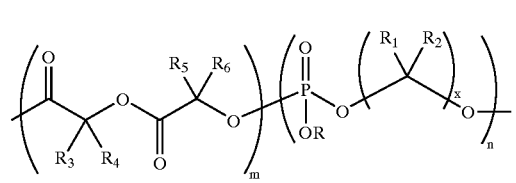

wherein

R is hydrogen, optionally substituted alkyl, optionally substituted $C_{2-12}$-alkenyl, optionally substituted heteroalkyl, optionally substituted $C_{2-12}$-alkynyl, or optionally substituted $C_{5-8}$-cycloalkyl;

$R^1$ and $R^2$ are each independently chosen from the group consisting of H, optionally substituted alkyl, optionally substituted $C_{2-12}$-alkenyl, optionally substituted heteroalkyl, optionally substituted $C_{2-12}$-alkynyl, and optionally substituted alkoxy;

x is 2, 3, or 4;

n and m are non-negative integers;

n+m is about 5 to about 2000; and m:n is between about 1:100 to about 100:1.

Biodegradable polymers of the invention including polymers according to formula I include polymers wherein each of m and n is about 10 to 1,000. Preferably each of m and n is about 10 to 500. Moreover, preferred polymers of the invention according to formula I or II include polymers wherein the molar ratio, m:n, is between about 1:100 to about 100:1, more preferably between about 1:50 to about 50:1 and particularly preferably between about 1:20 and 20:1.

Biodegradable polymers differ from non-biodegradable polymers in that they can be degraded during in vivo therapy. This generally involves breaking down the polymer into its monomeric subunits. In principle, the ultimate hydrolytic breakdown products of polymers suitable for use in the methods of the present invention should be biocompatible, non-toxic and easily excreted from a patient's body. However, the intermediate oligomeric products of the hydrolysis may have different properties. Thus,

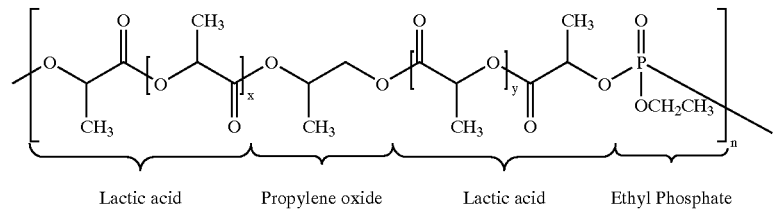

Preferred the biocompatible polymer suitable for use in microparticles or nanoparticles in the methods of the invention have one or more repeat units selected from phosphate, lactic acid, lactide, lactone, poly(ethylene oxide), and poly toxicology of a biodegradable polymer intended for implantation or injection, even one synthesized from apparently innocuous monomeric structures, is typically determined after one or more toxicity analyses.

The biodegradable polymer of the invention is preferably sufficiently pure to be biocompatible itself and remains biocompatible upon biodegradation. "Biocompatible" is defined to mean that the biodegradation products and/or the polymer itself are nontoxic and result in only minimal tissue irritation when instilled in the bladder or transported or otherwise localized to other tissues within a patient.

Weight-average molecular weights (Mw) typically vary from about 2,000 to about 200,000 daltons, preferably from about 2,000 to about 100,000 daltons and, most preferably, from about 2,000 to about 20,000 daltons. Number average molecular weights (Mn) can also vary widely, but generally fall in the range of about 1,000 to 100,000, preferably about 1,000 to 50,000 and, most preferably, from about 1,000 to about 10,000. For controlled release of a substance from a polymer matrix applications, preferred polymers of the invention have a Mw that is directly proportional to the specified length of time over which polymer degradation occurs, e.g., high Mw polymers undergo complete degredation more slowly than low Mw polymers.

Polymer microspheres and nanospheres comprising polymers as recited above are preferably formed by a water/oil/water (w/o/w) double emulsion technique. These microspheres have been shown to encapsulate a therapeutic agent such as a drug, protein, DNA or a mixture thereof. Micropheres comprising DNA prepared by a double emulsion technique typically retain much of the supercoiled DNA structure, and release the DNA over a period of weeks with minimal denaturation of the DNA. Furthermore, DNA and proteins encapsulated in microspheres are protected from enzymatic degradation, which should permit the release of biologically active DNA or protein from the microspheres for long periods of time following administration.

For the double emulsion method, the hydrophilic therapeutic agent is dissolved is water, emulsified in an organic solvent with or without an emulsifier, and then the resulting emuslion is further dispersed in an aqueous solution with an emulsifier, to create a water-in-oil-in-water mixture. The microspheres will then be prepared in a similar manner as described above.

Additionally preferred pharmaceutical compositions include a therapeutic agent encapsulated or otherwise dispersed in the polymer support material of a microparticle delivery vehicle. In a particular preparation method, the compositions can be isolated and purified by at least one and preferably all steps, involving isolating the microparticles by centrifugation; washing the microparticles with one or more wash cycles; and lyophilizing the microparticles.

In additional embodiments the pharmaceutical compositions can be prepared by any of the above-mentioned methods wherein the stabilizing agent is chosen from at least one of 0-polyethyleneoxides, polysorbates, polyvinylalcohols, polyvinylpyrrolidones, poly(N-2-hydroxypropyl methacrylamide)s, polyhydroxyethylmethacrylates, hydrophilic poly(aminoacid)s such as polylysine or polysaccharides. A particularly preferred polymer additive is polyvinylalcohol (PVA) with 0.5 to 10% w/w PVA blended into the homopolymer or more preferably 1 to 5% w/w PVA. A polymer blend with 2% PVA and 98% homopolymer is particularly preferred.

Preferred microparticles suitable for use in the methods of the present invention have an average particle size conducive to the transmission of the microparticles across the epithelial layer of the bladder. Typically the microparticles have an average particle size, measured by average diameter, of between about 250 nanometers and about 5 microns. More preferably, the microparticles have an average particle size of between about 500 nanometers and about 3 microns, or between about 600 nanometers and about 2 microns.

As used herein, the terms "microparticle," "microsphere," "nanoparticle" and "nanosphere" are intended to include nearly any particle with a mean diameter or particle size in the range of about 0.2 $\mu$m to about 25 $\mu$m, with a preference for particles with a mean diameter or particle size in the range of about 0.25 $\mu$m to about 5 $\mu$m, in the range of about 0.4 $\mu$m to about 4 $\mu$m, in the range of about 0.5 $\mu$m to about 3 $\mu$m or in the range of about 0.5 $\mu$m to about 2 $\mu$m which is composed of an approximately homogenous network of the support material. Preferred microparticle geometries are spherical, ellipsoidal and the like. Other polymeric devices included within the term microparticle include but are not limited to nanoparticles, micro or nanocapsules, hydrogels, gels and the like which are capable of encapsulating, or adsorbing or complexing compounds.

It is further intended that the terms microparticle, microsphere, nanoparticle or nanoshpere refer to particles prepared by an emulsion process that can encapsulate one or more discrete globules or droplets of a substance or a mixture of two or more substances during particle formation. The mass fraction of the encapsulated substance(s) is preferably about 0.1% to about 20% w/w of the microparticle.

In preferred embodiments of the present invention, microparticles suitable for use in administering a therapeutic agent to the lymph microparticles comprise at least about 0.1% by weight of the therapeutic agent. More typically the microparticles comprise at least about 0.25%, 0.5%, 1% or more by weight of the therapeutic agent. In particularly preferred embodiments the microparticle compositions comprise between about 0.1% and about 5% by weight or about 0.2% and about 5% by weight of the therapeutic agent.

It will be appreciated that the actual preferred amounts of therapeutic agent or other component used in a given composition will vary according to the therapeutic agent being utilized including the polymer system being employed, the mode of application, the particular site of administration, etc. Optimal administration rates for a given protocol of administration can be readily ascertained by those skilled in the art using conventional dosage determination tests conducted with regard to the foregoing guidelines.

As mentioned, the methods of the present invention include administering pharmaceutical compositions comprising a therapeutic agent encapsulated or otherwise dispersed in a polymer microparticle delivery vehicle, a more efficient application of the therapeutic agent is achieved, especially when the microparticle composition is localized to the bladder by instillation and the microparticles are then transported to a target tissue such as the lymph nodes within the patient. Preferably, microparticles instilled in the bladder are transpored across the epithelial layer of the bladder and then carried through the lymphatics to the lymph node.

In preferred methods of the invention at least 25%, 50%, 60%, 70%, 80%, or 90% of the therapeutic agent is delivered to the lymph node. More preferably at least 90% of the therapeutic agent contained within the microparticles instilled into the bladder are released in the lymph nodes.

In another embodiment of the present invention, a method is provided from modulating immune response of a patient. The method comprises the steps of:

instilling at least one microparticle with one or more therapeutic agents capable of modulating immune response to the bladder of a patient dispersed in the microparticle;

transporting the microparticles from the bladder to the lymph node; and releasing the encapsulated therapeutic agent to modulate the immune response of the patient.

In preferred methods of modulating the immune response of a patient the therapeutic agent can increase $T_H1$ immune response, increase $T_H2$ response or increase both the $T_H1$ and $T_H2$ responses. Typically the therapeutic agent is a DNA sequence encoding a antigen protein or a cytokine such that the DNA is incorporated into nearby cells after release from the microparticle. After incorporation into nearby cells, expression of the released DNA causes an immunological response as a function of the antigen protein or cytokine immunoadjuvant.

Microsphere constructs can be used to co-encapsulate immunoadjuvants, such as cytokines, which may act in a paracrine manner to significantly alter the immune response to the expressed antigen. To achieve a high local concentration of a DNA vaccine and cytokine additives, researchers have created plasmids that encode for both the antigen and the necessary cytokines. Plasmid DNA, cDNA, native DNA or any other form of DNA which is viable for the expression of the antigen protein or the immunoadjuvant such as a cytokine are suitable for use in the present invention.

In the present invention, DNA expressing for an antigen and for an immunoadjuvant such as a cytokine may be present in the same microsphere or nanosphere. Alternatively, a mixture of two or more microphere compositions may be administered wherein each microsphere composition comprises DNA expressing for a different protein, e.g., a mixture of two microsphere compositions may be instilled where one microsphere comprises a DNA expressing for the antigen and the other microsphere comprises DNA expressing for the cytokine. By decoupling the source of the DNA and the cytokines through microsphere delivery, the cytokine concentration profile can be varied independent from DNA expressing for the antigen such that the immunologic response can be controlled by varying the relative concentration of immunoadjuvant and antigen.

Methods of the present invention are suitable for any protein or DNA based vaccination method which induces either $T_H1$ $T_H2$ or a combination of $T_H1$ and $T_H2$ immunological responses. Methods are applicable for any illness or disease for which a vaccination is known or for which treatment is effected by systemic delivery of a therapeutic agent such as a small molecule drug, protein or DNA.

In preferred immune modulation methods of the invention, administration methods of the invention for delivering a therapeutic agent to the lymph nodes are suitable for delivering an therapeutic agent capable of modulating an immune response so that a patient's immune response is modulated. The lymph node is one of the primary sites for immune system stimulation; delivery of drugs, proteins, or DNA to these nodes results in the modulation of the immune response. After the microparticles are administered to the lymph nodes, they deliver their the therapeutic agent contained therein. Release of the therapeutic can be observed in by direct visualization of protein expression in cells of the lymph nodes, as well as indirect evidence through positive immune responses.

Mice receiving instilled microspheres comprising LacZ DNA expressed anti-beta-galactosidase specific immunoglobulin IgG1 or IgG2a responses. The presence of antibodies specific for beta-galactosidase was also an indirect measurement of gene expression; specific antibodies cannot be produced without the presence of the protein antigen. A positive antibody response was detected in all mice treated supporting the presence of a systemic release of IgG1 or IgG2a antibodies effected by localization of microparticles comprising LacZ DNA to the lymph nodes from the bladder.

In yet another aspect of the present invention, a method is provided for the systemic delivery of a therapeutic agent to a patient. The method comprises the steps of:

providing a microparticle or nanoparticle composition comprising at least one biocompatible instilling at least one microparticle comprising a therapeutic agent into a patient's bladder under conditions conducive to the transport of at least a portion of the microparticles across the epithelial layer of the bladder; and releasing at least a portion of the therapeutic agent from the microparticle such that the therapeutic agent is distributed systemically.

More preferred methods for the systemic administration of a therapeutic agent include methods wherein the microparticles are transported from the bladder, through the patient's lymphatic vessels, to at least one of the patient's lymph nodes. Particularly preferred methods for systemic administration of a therapeutic agent include those methods wherein at least 25% of the microparticles instilled in the patient's bladder are localized to the lymph nodes. More preferably, at least 30%, 40%, 50%, 60%, 70%, 75%, 80%, 85%, or 90% of the microparticles instilled in the patient's bladder are localized to the lymph nodes.

The adaptive immune system is composed of the cell-mediated and humoral arms, consisting of T-cells ($CD4^+$ and $CD8^+$) and B-cells, respectively. $CD8^+$ T-cells either kill infected cells directly (cytotoxic T-lymphocytes, or CTL's) or activate macrophages to destroy intracellular pathogens. $CD4^+$ T-helper cells (TH) can further be classified according to the responses they induce, e.g., a $T_H1$ response or a $T_H2$ response. $T_H1$ responses are mainly inflammatory and originate from T-cell recognition of intracellular antigens presented on MHC-I presentation molecules. $T_H1$ cells secrete paracrine signaling molecules called cytokines that activate macrophages to destroy the target cell's intracellular pathogens. $T_H1$ cells also stimulate B-cells to secrete specific antibody subclasses, e.g., IgG2a, to assist in the pathogen's destruction via activation of the complement system. $T_H2$ cells recognize extracellular antigens that are phagocytosed by cells, and mated with MHC-II molecules. The $T_H2$ cells act upon B-cells by secreting a different cytokine repertoire, causing the B-cells to increase production of a different set of antibodies (IgG1) that are necessary for killing certain extracellular pathogens.

Conventional protein vaccination is used throughout the world to protect against many infectious diseases, such as hepatitis and measles. However, protein vaccinations are ineffective in many cases, possibly because protein vaccines deliver the antigen extracellularly, so the immune response is primarily $T_H2$. One promising vaccination approach is the intramuscular injection of naked DNA, which has been shown to provide protection in animal models. As described in the previous section on gene therapy, the DNA is injected extracellularly, and taken up into the nucleus, where it expresses the protein antigen. This protein antigen is routed to acidic vesicles containing MHC-I molecules to be presented on the cells surface as an intracellular antigen, provoking a $T_H1$ immune response. Some antigen is also secreted extracellularly, where it is phagocytosed and presented on MHC-II molecules, which elicits a $T_H2$ response. In summary, these DNA vaccines induce both $T_H1$ and $T_H2$ responses, and may be effective for a wide variety of illnesses.

In addition to comprising a DNA sequence which encodes a protein antigen, preferred microparticle compositions suitable for use in the methods of the invention further comprise a cytokine or the DNA sequence encoding same. Preferred cytokines are not particularly limited, however cytokine signaling agents which are capable of boosting the immune response. Typically cytokine signaling agents will also shift the immune response to either a $T_H1$ (using interleukin-12 (IL-12) or interferon-gamnma (IFN-γ)), or $T_H2$ (via interleukin-4 (IL-4), interleukin-5 (IL-5), or interleukin-10 (IL-10)) response, which may be beneficial in certain diseases. For example, in a study of murine lung tumors, injection of naked DNA alone was ineffective in reducing primary lung metastases. In contrast, co-injection of naked DNA with the recombinant murine interleukin-12 dramatically decreased the number of primary lung metastases from more than 250 to around 10. Another study demonstrated a $T_H1$ response and a simultaneous lack of a $T_H2$ response was required for the clearance of a Leishmaniasis parasite infection. Immunization of mice with genes encoding for IL-12 generated a $T_H1$ immune response and increased protection against a Leishmaniasis parasite infection whereas IL-4 injections led to a $T_H2$ response and no protection.

In certain embodiments of the invention, methods of modulating an immune response can use microparticles comprising only a cytokine or a DNA sequence encoding same in the absence of a protein antigen or a DNA sequence encoding same. The cytokine is sufficient to illicit a desired immunological respons. For example, the granulocyte-monocyte colony-stimulating factor (GM-CSF) or IFN-γ, vaccination with an antigen is unnecessary; the cytokine alone is able to boost the immune response enough to have therapeutic value. Thus, inclusion of the appropriate cytokine either with or without a DNA vaccine may be beneficial for successful treatment.

Microspheres or nanospheres suitable for use in the methods of the present invention may include a protein or DNA vaccine, a cytokine signaling agent or DNA encoding a cytokine agent or a combination of a protein or DNA vaccine and a cytokine signaling agent or DNA encoding a cytokine agent. In other embodiments, a mixture of two microsphere compositions may be suitable for instillation wherein one microsphere comprises a DNA or protein based vaccine and another microsphere comprises a cytokine signaling agent for modulating immune response such that the ratio of cytokine and vaccine containing microspheres can be varied to modulate immunologic response.

Particle sizes of microparticles suitable for use in the methods of the invention are limited to particles which are taken up by the bladder tissue such as the submucosa and epithelial layer. While not being bound by theory, larger particles are generally less preferred than smaller particles because a higher percentage of large microparticles will be excreted from the bladder in the urine than small microparticles. Microsphere size has been shown to be extremely important in the microspheres' release rate, uptake, and adjuvanticity. Smaller microspheres have a larger surface area to volume ratio, which causes an increase in the release rate as compared to larger spheres.

In an illustrative example of particle size effecting uptake of the microparticle, in the oral delivery of microparticles which are taken up in the Peyer's Patches of the small intestine, microspheres must be less than 10 pm to be taken up by the Peyer's Patches (3). More specifically uptake is dependant upon particle size: 0.8 μm microspheres were efficiently taken up, 2.0 μm were taken up less efficiently (42). Microspheres larger than 5 μm tend to remain fixed in the Peyer's patches, providing a encapsulant depot, whereas microspheres smaller than 5 μm are transported within macrophages to the efferent lymphatics (3). An in vitro Peyer's Patch model (CACO-2 cells) demonstrated that 0.1 μm microparticles had 2.5 and 6 fold greater uptake than the 1 micron and 10 μm microparticles, on a weight basis, and more than a thousand fold increase on a number basis (43). In addition to uptake by specific tissues, individual cells, such as macrophages in the liver, lung, spleen, and bone marrow engulf microparticles under 10 μm and degrade them within days (44). Thus, controlling the size of microspheres may permit a targeting of specific cell and tissue types.

Typically a polymer is dissolved in an organic solvent, a hydrophilic therapeutic agent is dissolved in water and a hydrophobic therapeutic agent (if any) is co-dissolved with the polymer in the organic solvent. An water/oil emulsion is formed by mixing the immiscible liquids with sever agitation such as sonication or vortexing. The emulsion is typically added to a second aqueous solution of a salt and an emulsifying agent, e.g., an aqueous solution of sodium chloride and poly(vinyl alcohol), with additional sonication or other means of violent agitation. Microspheres are isolated by evaporation of the organic solvent, washing and drying the solid microspheres. The size of the microspheres is generally controlled by controlling the agitation of the emulsion. Typically the greater the amount of agitation the smaller the resultant microspheres. The uptake of therapeutic agent can be determined by measuring residual therapeutic agent present in the supernatant. The difference between total therapeutic agent added and the residual therapeutic agent in the supernatant is about the same as the quantity of therapeutic agent dispersed in the microspheres.

The differences in tissue and cell uptake have consequences on the subsequent immune response. In a Hepatitis B guinea pig model, small (1–10 μm) microspheres possessed an early, but brief adjuvant effect, whereas larger (20–60 μm) microspheres remained at the injection site until degradation into smaller fragments that could then be engulfed by macrophages. This resulted in a delayed but enhanced antibody response. For a DNA vaccine, intramuscular immunization with 0.3 μm, 1 μm, and 30 μm microspheres led to correspondingly lower antibody titers, with 30 μm microspheres causing an unmeasurable response. Thus, it is desirable to control the size of microspheres fabricated for gene therapy.

Figure 6C:
FIG. 6C is a TEM image of a DNA-containing nanosphere engulfed in a bladder vesicle.
Figure 6B:
FIG. 6B is a TEM image of a DNA-containing nanosphere in the invaginations of the bladder.
Figure 6A:
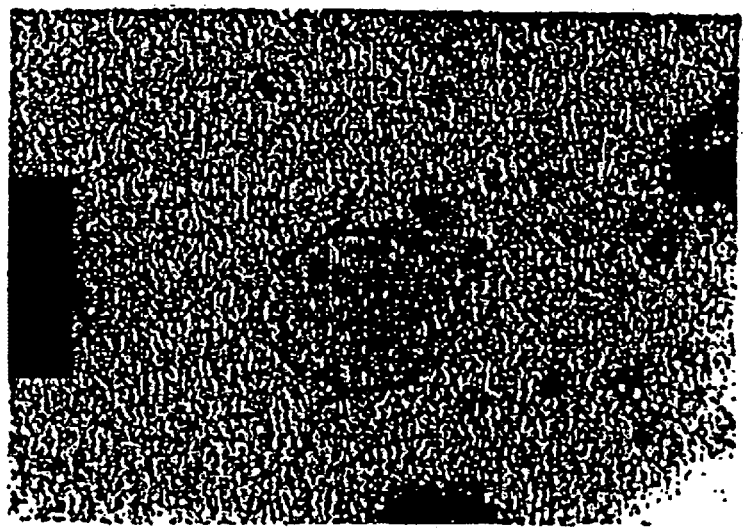
FIG. 6A is a TEM image of a DNA-containing nanosphere.

Confocal microscopy of microspheres containing ethidium bromide-labeled DNA revealed an apparently homogeneous dispersion of DNA throughout the microsphere (FIG. 6). Salmon sperm DNA loading levels of up to 4.8% were achieved, with encapsulation efficiencies greater than 90% (LacZ loading levels were about 1.9%). Microspheres with number average sizes ranging from 350 nm to 25 μm were obtained using variations of a w/o/w double emulsion technique. For the primary emulsion, increasing the sonication time above 6 seconds yielded a more uniform size distribution. Decreasing the sonication power decreased the size of the microspheres; this was consistent with the increase in DNA damage at lower power. When the secondary emulsion was prepared with a vortexer, faster rates decreased the microsphere size. A stirring rate of 700 RPM yielded the narrowest size distribution (number average near 11 μm), with slower and faster stirring rates leading to both larger and smaller microspheres; it appeared that the most homogeneous mixing occurred at 700 RPM. None of the parameters mentioned above resulted in an average microsphere size below 5 μm, however, by changing the method of secondary emulsion preparation from vortexing to sonication, the average microsphere size was reduced to about 440 nm. These nano-size microspheres (nanospheres) did not aggregate over time (for over one month), as measured by dynamic light scattering. Variation of the agitation method and the vigorousness of agitation can be varied to control the average particle size of microparticles and nanoparticles generated by the w/o/w double emulsion methods of the invention.

Figure 3B:
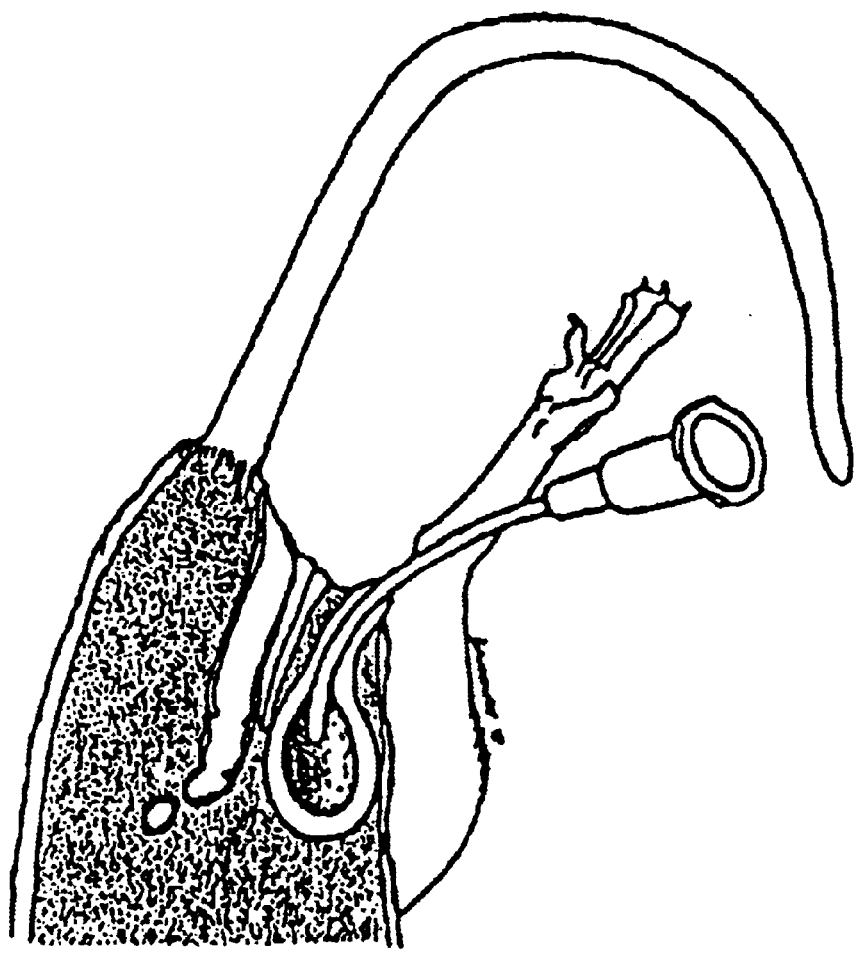
FIG. 3 is an illustration of the instillation procedure for depositing microspheres into the bladder of a mouse through a catheter.
Figure 3A:
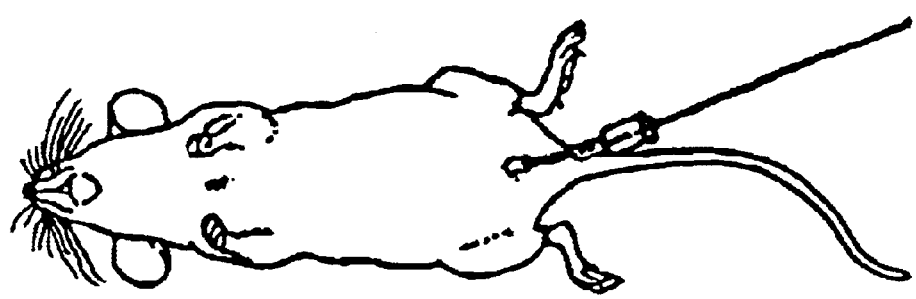

The rate of uptake of the small and large microspheres into the bladder proper varied, and was measured using the following the analytical method described in Example 6. Following bladder instillation of the pink microspheres, e.g, microparticles comprising Nile-Red dye, the mice were closely monitored and their urine was collected for four hours. At early times following instillation of the small microspheres, the urine contained a small fraction of pink microspheres originally instilled, whereas mice urinating after 30 minutes had yellow urine and few traces of the pink microspheres. In contrast, the urine of mice instilled with the large microspheres was filled with a sixteen-fold higher concentration of dye-labeled microspheres in their urine, as measured fluorometrically (FIG. 3). Thus, the rate of uptake of the small microspheres appeared to be several-fold faster than the large microspheres. Additionally, more than 90% of the administered dose of the smaller spheres were taken up, and was done so within 3 hours following instillation. It should be noted here that this level of uptake is extremely high, and is one of the primary advantages affording by this method of delivery.

In an illustrative example of the methods of the invention, the uptake and transport of nanoparticles comprising marker gene LacZ (encoding beta-galactosidase (beta-gal)) from the bladder was observed following noninvasive bladder instillation of the nanoparticles into female Balb/c mice. Three hours after instillation of the nanoparticles into the bladder, 90% of the administered particles were taken up by the bladder tissue, with few particles remaining in the urine. Confocal analysis revealed nanoparticles in the submucosa of the bladder 30 minutes following instillation. Particles were not observed in the in the submucosa at later time points, e.g., at 1.5, 3 or 48 hours and immunohistochemical beta-gal staining showed no detectable transfection of cells in the bladder with the LacZ gene. Nanoparticles were observed in the draining lymph node at 3 hours. In comparison, a positive stain was observed in draining lymph node cells at 48 hours. Serum IgG1 and IgG2a antibodies were detected by ELISA two weeks following nanoparticle instillation. These studies demonstrate that DNA-polyphosphoester nanoparticles are taken up into the bladder and are transported to the draining lymph nodes, causing transfection and immune response generation.

As used herein, "alkyl" is intended to include branched, straight-chain and cyclic saturated aliphatic hydrocarbon groups including alkylene, having the specified number of carbon atoms. Examples of alkyl include, but are not limited to, methyl, ethyl, n-propyl, i-propyl, n-butyl, s-butyl, t-butyl, n-pentyl, and s-pentyl. Alkyl groups typically have 1 to about 16 carbon atoms, more typically 1 to about 20 or 1 to about 12 carbon atoms. Preferred alkyl groups are $C_1$–$C_{20}$ alkyl groups, more preferred are $C_{1-12}$-alkyl and $C_{1-6}$-alkyl groups. Especially preferred alkyl groups are methyl, ethyl, and propyl.

As used herein, "heteroalkyl" is intended to include branched, straight-chain and cyclic saturated aliphatic hydrocarbon groups including alkylene, having the specified number of carbon atoms and at least one heteroatom, e.g., N, O or S. Heteroalkyl groups will typically have between about 1 and about 20 carbon atoms and about 1 to about 8 heteroatoms, preferably about 1 to about 12 carbon atoms and about 1 to about 4 heteroatoms. Preferred heteroalkyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alylthio groups having 1, 2, 3, or 4 carbon atoms are particularly preferred. Prefered alkylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkylsulfinyl groups having 1, 2, 3, or 4 carbon atoms are particularly preferred. Preferred alkylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alylsulfonyl groups having 1, 2, 3, or 4 carbon atoms are particularly preferred. Preferred aminoalkyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkyl groups having 1, 2, 3, or 4 carbon atoms are particularly preferred.

As used herein, "heteroalkenyl" is intended to include branched, straight-chain and cyclic saturated aliphatic hydrocarbon groups including alkenylene, having the specified number of carbon atoms and at least one heteroatom, e.g., N, O or S. Heteroalkenyl groups will typically have between about 1 and about 20 carbon atoms and about 1 to about 8 heteroatoms, preferably about 1 to about 12 carbon atoms and about 1 to about 4 heteroatoms. Preferred heteroalkenyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alkenylthio groups having 1, 2, 3, or 4 carbon atoms are particularly preferred. Prefered alkenylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkenylsulfinyl groups having 1, 2, 3, or 4 carbon atoms are particularly preferred. Preferred alkenylsulfonyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkenylsulfonyl groups having 1, 2, 3, or 4 carbon atoms are particularly preferred. Preferred aminoalkenyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkenyl groups having 1, 2, 3, or 4 carbon atoms are particularly preferred.

As used herein, "heteroalkenyl" is intended to include branched, straight-chain and cyclic saturated aliphatic hydrocarbon groups including alkynylene, having the specified number of carbon atoms and at least one heteroatom, e.g., N, O or S. Heteroalkenyl groups will typically have between about 1 and about 20 carbon atoms and about 1 to about 8 heteroatoms, preferably about 1 to about 12 carbon atoms and about 1 to about 4 heteroatoms. Preferred heteroalkenyl groups include the following groups. Preferred alkylthio groups include those groups having one or more thioether linkages and from 1 to about 12 carbon atoms, more preferably from 1 to about 8 carbon atoms, and still more preferably from 1 to about 6 carbon atoms. Alkylthio groups having 1, 2, 3, or 4 carbon atoms are particularly preferred. Prefered alkynylsulfinyl groups include those groups having one or more sulfoxide (SO) groups and from 1 to about 12 carbon atoms, more preferably from 1 to about 8 carbon atoms, and still more preferably from 1 to about 6 carbon atoms. Alkynylsulfinyl groups having 1, 2, 3, or 4 carbon atoms are particularly preferred. Preferred alkynylsulfinyl groups include those groups having one or more sulfonyl ($SO_2$) groups and from 1 to about 12 carbon atoms, more preferably from 1 to about 8 carbon atoms, and still more preferably from 1 to about 6 carbon atoms. Alkynylsulfonyl groups having 1, 2, 3, or 4 carbon atoms are particularly preferred. Preferred aminoalkynyl groups include those groups having one or more primary, secondary and/or tertiary amine groups, and from 1 to about 12 carbon atoms, more preferably from 1 to about 8 carbon atoms, and still more preferably from 1 to about 6 carbon atoms. Aminoalkynyl groups having 1, 2, 3, or 4 carbon atoms are particularly preferred.

As used herein, "cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "($C_{3-6}$ cycloalkyl)$C_{1-4}$ alkyl", as defined above, the point of attachment is on the alkyl group. This term encompasses, but is not limited to, cyclopropylmethyl, cyclohexylmethyl, cyclohexylmethyl.

As used here, "alkenyl" is intended to include hydrocarbon chains of straight, cyclic or branched configuration, including alkenylene, and one or more unsaturated carbon-carbon bonds which may occur in any stable point along the chain, such as ethenyl and propenyl. Alkenyl groups typically will have 2 to about 12 carbon atoms, more typically 2 to about 12 carbon atoms.

As used herein, "alkynyl" is intended to include hydrocarbon chains of straight, cyclic or branched configuration, including alkynylene, and one or more triple carbon-carbon bonds which may occur in any stable point along the chain, such as ethynyl and propynyl. Alkynyl groups typically will have 2 to about 20 carbon atoms, more typically 2 to about 12 carbon atoms.

As used herein, "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Typical haloalkyl groups will have 1 to about 16 carbon atoms, more typically 1 to about 12 carbon atoms.

As used herein, "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 16 carbon atoms, more typically 1 to about 12 carbon atoms.

"Prodrugs" are intended to include any covalently bonded carriers which release the active parent drug according to formula I in vivo when such prodrug is administered to a mammalian subject. Prodrugs of a compound are prepared by modifying functional groups present in the drug compound in such a way that the modifications are cleaved, either in routine manipulation or in vivo, to the parent compound.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

As used herein, the term "aliphatic" refers to a linear, branched, cyclic alkane, alkene, or alkyne. Preferred aliphatic groups in the poly(phosphoester-co-amide) polymer of the invention are linear or branched and have from 1 to 20 carbon atoms.

As used herein, the term "aryl" refers to an unsaturated cyclic carbon compound with $4n+2\pi$ electrons where n is a non-negative integer, about 5–18 aromatic ring atoms and about 1 to about 3 aromatic rings.

As used herein, the term "heterocyclic" refers to a saturated or unsaturated ring compound having one or more atoms other than carbon in the ring, for example, nitrogen, oxygen or sulfur.

A typical in vitro toxicity assay for biocompatibility of biodegradable polymers suitable for use in the methods of the invention would be performed with live carcinoma cells, such as GT3TKB tumor cells, in the following manner:

200 $\mu$L of various concentrations of suspensions of the test monomer or polymers are placed in 96-well tissue culture plates seeded with human gastric carcinoma cells (GT3TKB) at $10.^4$/well density. The degraded polymer products are incubated with the GT3TKB cells for 48 hours. The results of the assay can be plotted as % relative growth vs. concentration of degraded polymer in the tissue-culture well.

The polymer of the invention can also comprise additional biocompatible monomeric units so long as they do not interfere with the biodegradable characteristics desired. Such additional monomeric units may offer even greater flexibility in designing the precise release profile desired for targeted drug delivery or the precise rate of biodegradability desired for structural implants such as for orthopedic applications. Examples of such additional biocompatible monomers include the recurring units found in polycarbonates; polyorthoesters; polyamides; polyurethanes; poly (iminocarbonates); and polyanhydrides.

The polymers of the invention are usually characterized by a release rate of the therapeutic agent in vivo that is controlled at least in part as a function of hydrolysis of the phosphoester bond of the polymer during biodegradation. Additionally, the therapeutic agent to be released may be conjugated to the phosphorus sidechain R' to form a pendant drug delivery system. Further, other factors are also important.

The life of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be.

The therapeutic agent of the invention can vary widely with the purpose for the composition. The agnet(s) may be described as a single entity or a combination of entities. The delivery system is designed to be used with therapeutic agents having high water-solubility as well as with those having low water-solubility to produce a delivery system that has controlled release rates. The terms "therapeutic agent" and "biologically active substance" include without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of useful therapeutic agents and biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, antigenic materials, and prodrugs.

Specific examples of useful therapeutic agents and biologically active substances from the above categories include: (a) anti-neoplastics such as androgen inhibitors, antimetabolites, cytotoxic agents, immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (o) antigenic materials, partricularly those useful in vaccine applications.

Preferably, the therapeutic agent or biologically active substance is selected from the group consisting of DNA, polysaccharides, growth factors, hormones, anti-angiogenesis factors, interferons or cytokines, and pro-drugs. In a particularly preferred embodiment, the therapeutic agent is a DNA vaccine comprising a DNA sequence encoding an antigen, a DNA sequence encoding a cytokine or a mixture of DNA sequences encoding an antigen and a cytokine.

The therapeutic agents are used in amounts that are therapeutically effective. While the effective amount of a therapeutic agent will depend on the particular material being used, amounts of the therapeutic agent from about 1% to about 65% have been easily incorporated into the present delivery systems while achieving controlled release. Lesser amounts may be used to achieve efficacious levels of treatment for certain therapeutic agents.

In addition, the polymer composition of the invention can also comprise polymer blends of the polymer of the invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for structural implants such as for orthopedic applications. Examples of such additional biocompatible polymers include other polycarbonates; polyesters; polyorthoesters; polyamides; polyurethanes; poly(iminocarbonates); and polyanhydrides.

Pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

In its simplest form, a biodegradable therapeutic agent delivery system consists of a dispersion of the therapeutic agent in a polymer matrix. The therapeutic agent is typically released as the polymeric matrix biodegrades in vivo into soluble products that can be excreted from the body.

As a drug delivery device, the polymer compositions of the invention provide a polymeric matrix capable of sequestering a biologically active substance and provide predictable, controlled delivery of the substance. The polymeric matrix then degrades to non-toxic residues.

The following examples are illustrative of the invention. All documents mentioned herein are incorporated herein by reference.

General Experimental Details

Sheared salmon sperm DNA was purchased from 5 Prime→3 Prime. The poly(phosphoester) poly(D,L-lactide-co-ethyl phosphate) P(DAPG-EOP), a chain-extended poly (lactic acid) with $M_W$ and $M_n$ near 20 kD and 7 kD, respectively, was synthesized by Dr. Jie Wen by a process described above.

EXAMPLE 1

Microspheres comprising a biocompatible polymer and a therapeutic agent were prepared via variations of a water/oil/water (w/o/w) double-emulsion technique (FIG. 1). An aqueous solution of LacZ DNA (2 mg) dissolved in 200 μL water was added to a polymer (100 mg) selected from P(DAPG-EOP), poly(lactic acid) (PLA), or poly(lactic-co-glycolic acid) 50:50 mixture of lactic acid:glycolic acid (PLGA 50:50) dissolved in 1 mL methylene chloride and sonicated to form the primary water/oil (w/o) emulsion. This mixture was added to 5 mL of 5% NaCl, 1% poly(vinyl alcohol) (PVA) and either sonicated or vortexed to form the secondary (w/o/w) emulsion. This was then added to 40 mL of 5% NaCl, 0.3% PVA, and stirred for 3 hours at room temperature to evaporate the methylene chloride. The microspheres were washed 3 times with water and lyophilized for storage. The LacZ concentration in the supernatant before the first wash was measured fluorometrically to determine the DNA encapsulation efficiency and loading level. The encapsulation efficiencies and loading levels are shown below (Table 2)

TABLE 2

Encapsulation efficiencies and loading levels of LacZ-containing microspheres

| Polymer | Encapsulation efficiency (%) | Loading level (%) |
|---|---|---|
| PDAPG-EOP | 96 | 2.0 |
| PLGA 50:50 | 44 | 0.93 |
| PLA | 15 | 0.31 |

EXAMPLE 2

Figure 2B:
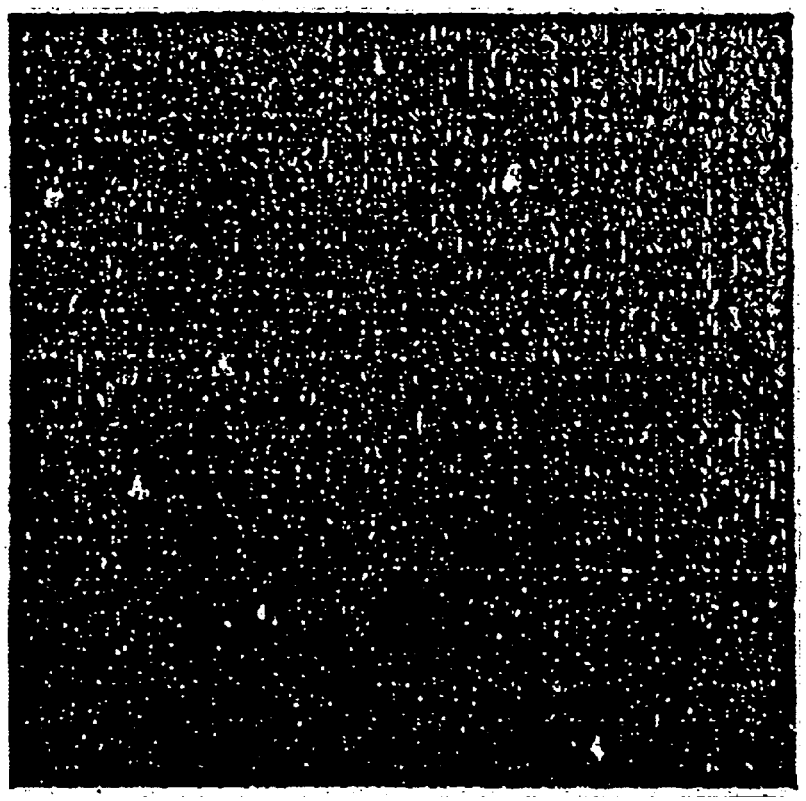
FIG. 2B is a confocal micrograph of P(DAPG-EOP) microspheres containing salmon sperm DNA labeled with ethidium bromide fabricated using a sonicated second emulsion step (scale: 100 $\mu$m×100 $\mu$m)
Figure 2A:
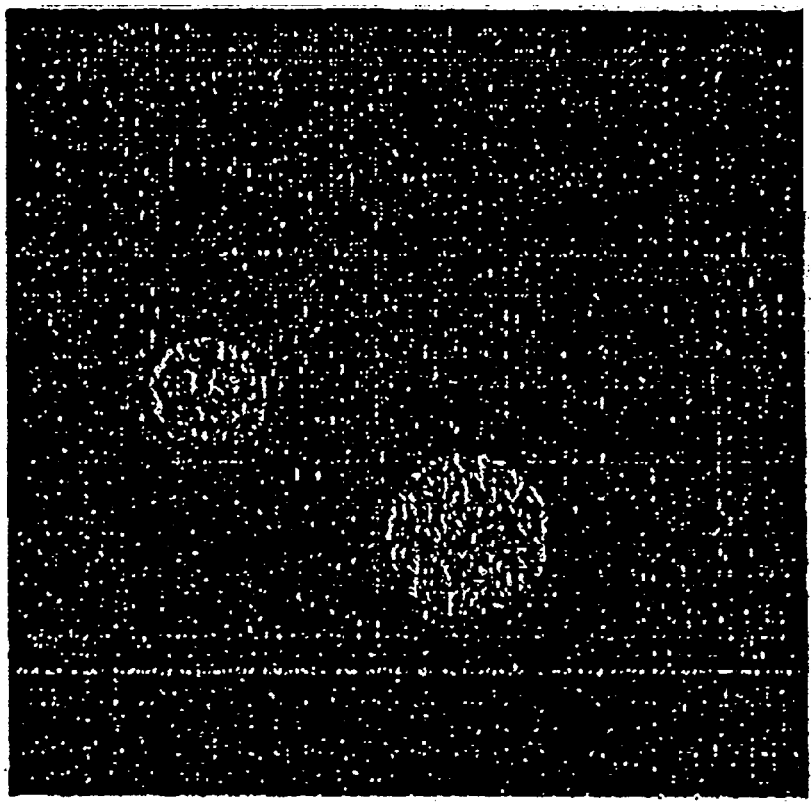
FIG. 2A is a confocal micrograph of P(DAPG-EOP) microspheres containing salmon sperm DNA labeled with ethidium bromide fabricated using a vortexed second emulsion step (scale: 100 $\mu$m×100 $\mu$m)

For Confocal microscopy, DNA was labeled with ethidium bromide (excitation=518 nm, emission=605 nm), washed three times with cold ethanol. The microspheres were prepared as above. Following the microsphere preparation, the samples were alternately washed and centrifuged three times with water; the supernatant was clear, whereas the pellet of microspheres was bright pink. The microspheres were resuspended in water, placed on a microscope slide, covered with a cover slip, and imaged using the argon laser exciting at 514 nm. See FIG. 2 for micrographs of P(DAPG-EOP) microspheres containing salmon sperm DNA labeled with ethidium bromide.

EXAMPLE 3

For visualization with fluorescence microscopy, P(DAPG-EOP) was labeled with Nile Red, a hydrophobic, fluorescent dye (excitation maximum at 536 nm, emission maximum at 610 nm). Small and large P(DAPG-EOP) microspheres were prepared as above, with the following modification: approximately 1 mg Nile Red (Molecular Probes, Inc., Portland, Oreg.) dye (excitation=560, emission=610) was dissolved in the methylene chloride along with the polymer. The DNA dissolved in water was added to this solution and sonicated at 20% power for 15 seconds to form the primary emulsion. To make the small microspheres, 5 mL of 5% NaCl+1% PVA was added to the primary emulsion and sonicated at 20% power for 15 seconds. For the large microspheres, 5 mL of 5% NaCl+1% PVA was added to the primary emulsion and homogenized (Polytron PT1200 homogenizer) on speed 6 for 15 seconds. For both small and large microspheres, the secondary emulsion was added to 40 mL 5% NaCl+0.3% PVA stirring at 700 RPM. The mixture was allowed to stir for 3 hours to evaporate the methylene chloride and followed by 3 washes and centrifugation (10 minutes at 10,000 RPM for the small spheres, 5 minutes at 2000 RPM for the large spheres) to collect the microspheres. The microspheres were stored in water at 4° C. until use.

EXAMPLE 4

Microspheres containing LacZ were prepared in two size ranges: one had a median size of 600 nm ("nanospheres"), while the second ranged in size from 1–15 μm, with a median number size near 5 μm ("microspheres"). In order to provide reliable tracking, the dye needed to remain associated with the polymer and continue to be fluorescent at low pH, as the microspheres were subjected to the slightly acidic environment of the urinary bladder. Experiments showed that the hydrophobic dye remain firmly associated with the polymer for at least one week in water at 4° C., because no dye was found in the supernatant following centrifugation for 5 minutes at 10,000 RPM. Incubation of the dye with 10N HCl did not alter the dye's fluorescent properties. Furthermore, the dye remained associated with the polymer and retained its fluorescent properties when incubated with naïve mouse urine in vitro for extended periods at room temperature.

EXAMPLE 5

For bladder instillation, animals were rendered unconscious with Metofane (Schering-Plough, N.J.) and laid on their back. The mouse clitoris was gently held with forceps, while the urethra was catheterized until the anterior wall of the bladder was encountered (FIG. 3). The bladder was palpated to remove any urine. Eighty μL of microsphere solution containing approximately 1.25 mg microspheres (25 μg LacZ DNA) was instilled, followed by removal of the catheter. The mice were observed until full consciousness returned.

EXAMPLE 6

Figure 4:
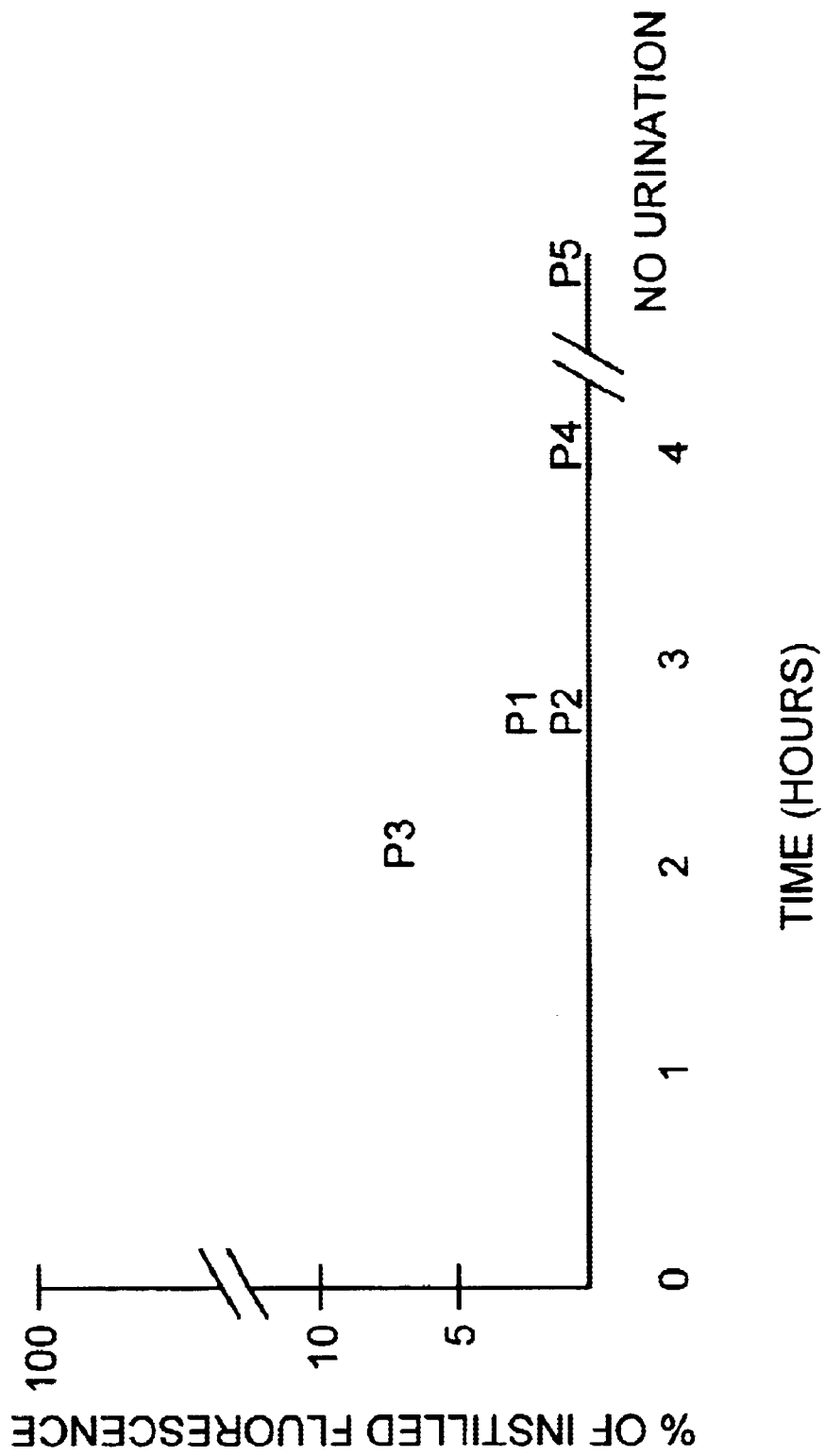
FIG. 4 is a table of uring fluorescence resulting from microspheres excreted in the urine after instillation with 80 $\mu$L of Nile-Red-labeled microspheres over a four hour period.

Microparticles of P(DAPG-EOP) comprising Nile Red dye were instilled via a catheter into the bladder of a plurality of mice. Urine was collected over a period of four hours and the concentration of dye including both free dye molecules and dye dispersed in microparticles was measured by fluoroscopy. For small microparticles, e.g., particles with an average size less than 1 micron, dye was observed in the urine only during the first 30 minutes. Dye was observed in the urine of mice instilled with larger micropartices for up to three hours after instillation and the concentration of dye was up to 16 fold greater than in the urine of mice instilled with smaller microparticles. The dye concentration in urine for mice instilled with larger microparticles was measured fluorometrically (FIG. 4). More than 90% of the administered dose delivered by small microspheres is transported to the lymph node within three hours of instillation.

EXAMPLE 7

Figure 5B:
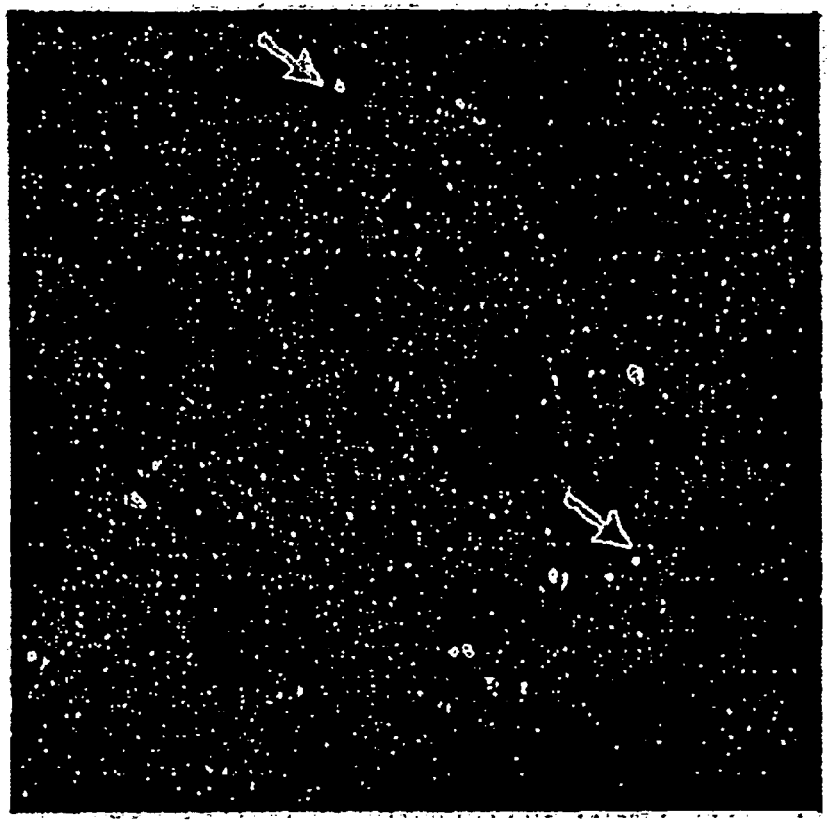
FIG. 5B is a confocal image of the lymph node taken 3 hours after instillation at 40× magnification.
Figure 5A:
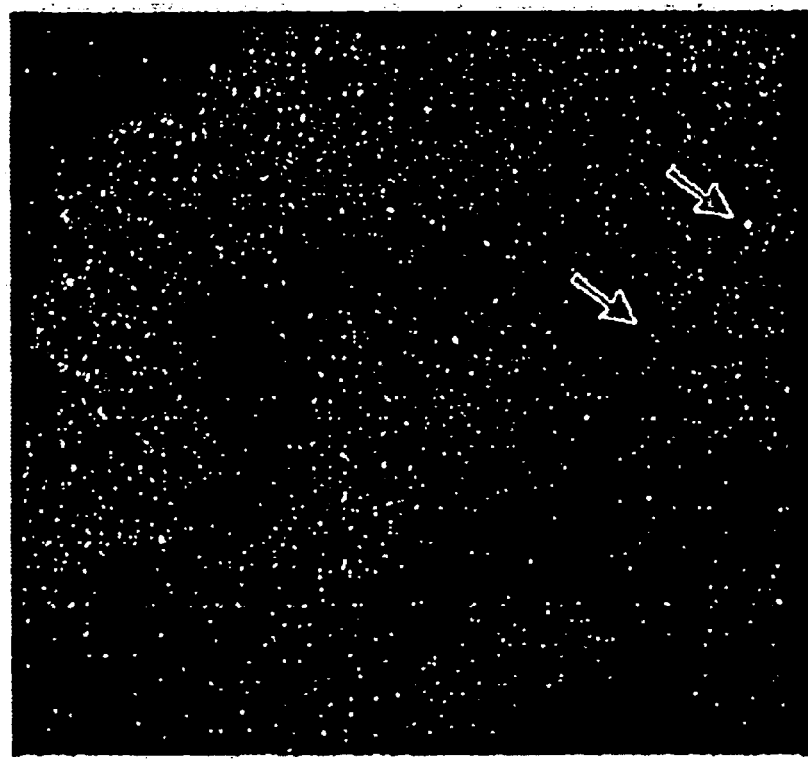
FIG. 5A is a confocal image of the bladder taken 30 minutes after instillation at 40× magnification.

Standard confocal microscopic analysis of organ sections of mice sacrificed at 30 minutes, 90 minutes, 3 h and 48 hours after bladder instillation was performed. For the small microspheres, after 30 minutes, microspheres were visible in the bladder lumen and along the mucosal cells (FIG. 5A). No microspheres were observed in the bladder at any of the later time points. This was consistent with the findings of the Example 6, where few nanospheres were found in the urine. The microspheres were not found in lung, spleen, or liver sections at any time point, but were seen in the lymphatics at 90 minutes and in lymph nodes at the 3-hour time point (FIG. 5B).

EXAMPLE 8

To examine the mechanism of uptake of the nanospheres from the bladder lumen, P(DAPG-EOP) nanospheres containing DNA were instilled into the bladders of female Balb/c mice. These mice that were sacrificed at either 7 or 20 minutes and their bladders prepared for TEM (500 nm sections). FIG. 6 provides TEM images of mouse bladder with microparticles contained therein.

EXAMPLE 9

Figure 7:
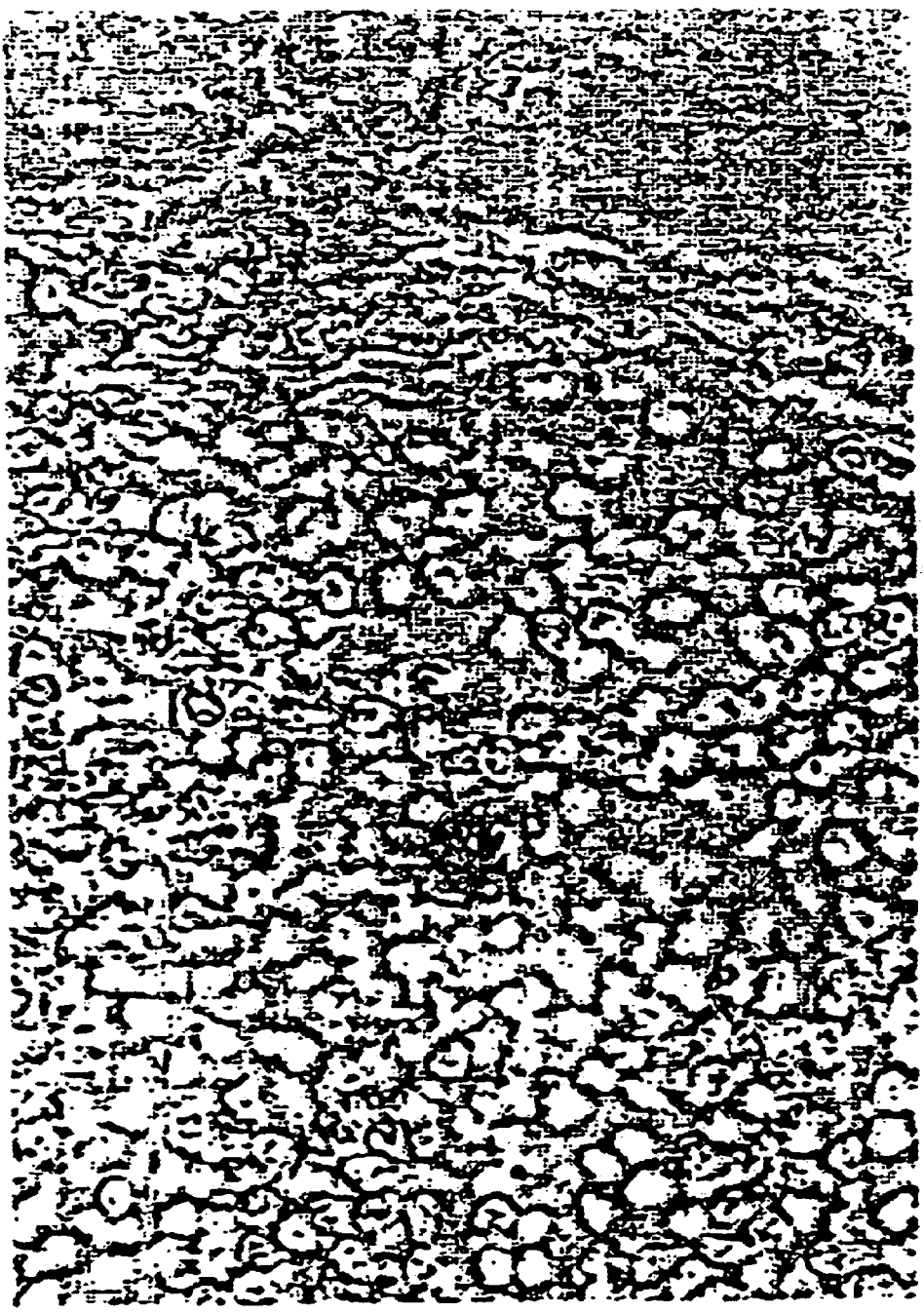
FIG. 7 is an image showing immunohistochemical staining for beta-galactosidase in the lymph node 48 hours after instillation.
Figure 8:
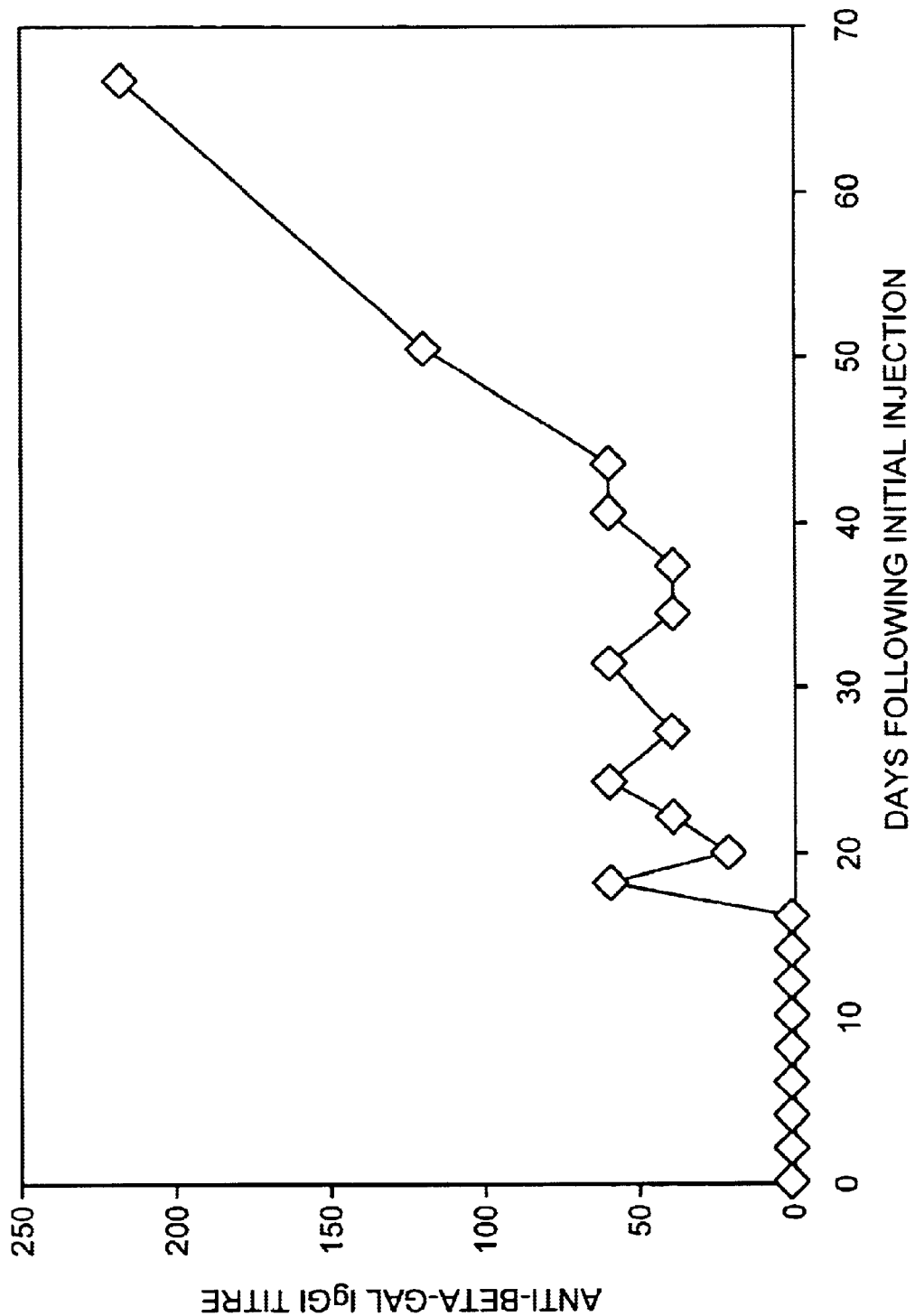
FIG. 8 is a table of anti-beta-galactosidase IgG1 antibody response to microspheres containing LacZ DNA instilled through the bladder at day 0, followed by a booster instillation at day 35 (n=4 mice)

Following sacrifice of the mice and after the appropriate organs are removed (spleen, lung, liver, lymph nodes, bladder), the organs were frozen on dry ice and stored at −80° C. until they were sliced into 10 micron sections on a cryomicrotome. The sections were placed on Superfrost Plus® (Fisher), brought to room temperature, and rehydrated with 0.1N Tris-HCl (pH 7.6) for 10 minutes. After permeabilization with 0.1% Triton in Tris-HCl buffer, the slides were washed with Tris-HCl and the endogenous peroxidase blocked with 3% hydrogen peroxide. Three more Tris-HCl washes were followed by incubation with 0.01% Trypsin-EDTA for 1 hour. The addition of with BSA/Tween 20 solution (2% BSA, 0.05% Tween 20) and two BSA/Tween 20 was were succeeded by incubation with the primary rabbit antibody at 1:1000 dilution in Tris-HCl in a humidified chamber for 1 hour. After washing twice with Tris-HCl, the slides were blocked with 5% nonfat milk in Tris-HCl. The secondary antibody at 1:1000 dilution were added after a BSA/Tris-HCl wash. After a 45-minute incubation and three Tris-HCl washes, the horseradish peroxidase-labeled secondary antibody were developed with True Blue (KPL) substrate in the dark for 7 minutes and counterstained with nuclear fast red after a wash with water. The slides were successively dehydrated in 75%, 95%, 100%, and 100% ethanol, followed by xylene dehydration and air drying. Clarion mounting media were used to fix the coverslip to the slide. This immunohistochemical staining for beta-galactosidase revealed expression in the lymph nodes of mice (FIG. 7).

EXAMPLE 10

Five mice received were instilled with eighty μL of microsphere solution containing approximately 1.25 mg nanospheres (25 μg LacZ DNA). The mice were bled every other day for about 3 weeks, followed by several more bleedings for up to 40 days following instillation. Anti-β-galactosidase-specific immunoglobulin G (IgG1 and IgG2a) levels in serum will be measured using an ELISA assay. A 96-well EIA plate (Costar) was coated overnight at 4° C. with 50 μl of 50 μg/mL β-gal in PBS and blocked with 4% bovine serum albumin (BSA, Sigma Chemical) and 4% goat serum (Life Sciences). Serum samples were initially diluted 1:80 with PBS supplemented with 0.05% Tween 20 (Sigma Chemical) (PBS-T), followed by serial dilutions thereafter. Fifty μL of sample or standard was added to the coated and blocked plate and incubated for 2 hr at 37° C. Following 3 washings with PBS-T, 50 μL of 1:5000 biotinylated IgG1 or 1:10,000 biotinylated IgG2a peroxidase-conjugated secondary antibody (goat-anti-mouse IgG, Boehringer Mannheim) was incubated for another 2 hours at 37° C. The plates were washed again with 50 μl PBS-T and streptavidin-horseradish peroxidase was added and the plates were incubated for 25 minutes at 37° C. After another PBS-T wash cycle, 50 μL Turbo-TMB substrate was added and the plates incubated for 10 minutes at room temperature. Fifty μL of 0.5M $H_2SO_4$ was added to quench the reaction. The absorbance at 450 nm was read on a plate reader. Anti-beta-galactosidase IgG1 antibody response to nanospheres containing LacZ DNA instilled through the bladder at day 0, followed by a booster instillation at day 35 (n=4 mice). The pre-instillation antibody response (1 week prior to instillation) was 0 for all 4 mice.

EXAMPLE 11

Figure 9:
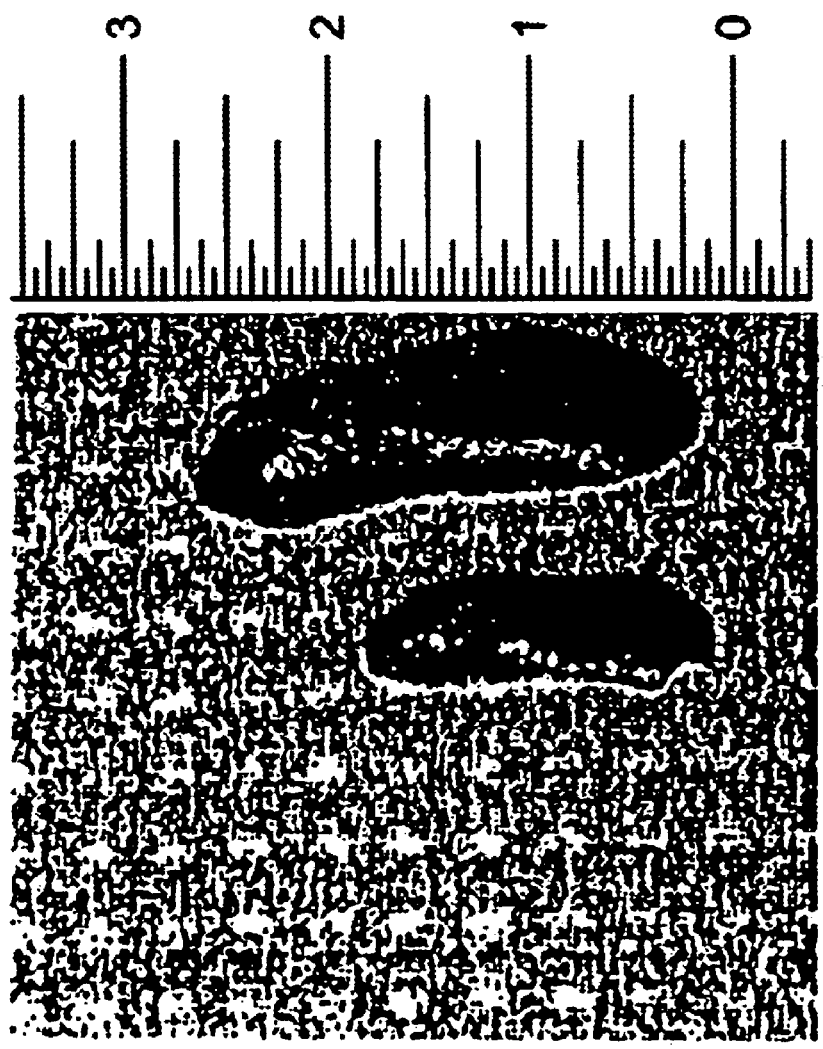
FIG. 9 is an image comparing mice spleens collected from a mouse receiving microspheres containing GM-CSF DNA (right) and a mouse receiving PBS.

After instillation of mice with a P(DAPG-EOP) polymeric nanosphere containing DNA encoding granulocyte-monocyte colony stimulating factor (GM-CSF), we weighed the spleens at 4 weeks following instillation. The spleen weights were 40% higher in mice receiving nanospheres versus mice receiving phosphate-buffered saline (p-value<0.05) indicating immune response to instilling nanoparticles comprising biologically active substance into the bladder (FIG. 9).

The following publications and any patent or publication referred to herein is hereby incorporated by reference.
1. Werthman, P. E., K. E. Drazan, J. T. Rosenthal, R. Khalili, and A. Shaked, *Adenoviral-p53 gene transfer to orthotopic and peritoneal murine bladder cancer*. Journal of Urology, 1996. 155(2): p. 753–756.
2. Frangos, D. N., J. J. Killion, D. Fan, R. Fishbeck, A. C. von Eschenbach, and I. J. Fidler, *The development of liposomes containing interferon alpha for the intravesical therapy of human superficial bladder cancer*. Journal of Urology, 1990. 143(6): p. 1252–6.
3. Jacobi, G. H. and K. H. Kurth, *Studies on the intravesical action of topically administered G3H-doxorubicin hydrochloride in men: plasma uptake and tumor penetration*. J Urol, 1980. 124(1): p. 34–7.
4. Jones, D. H., J. C. Clegg, and G. H. Farrar, *Oral delivery of micro-encapsulated DNA vaccines*. Developments in Biological Standardization, 1998. 92: p. 149–55.
5. Roy, K., H. Q. Mao, S. K. Huang, and K. W. Leong, *Oral gene delivery with chitosan—DNA nanoparticles generates immunologic protection in a murine model of peanut allergy*. Nature Medicine, 1999. 5(4): p. 387–91.
6. Kofler, N., C. Ruedl, C. Rieser, G. Wick, and H. Wolf, *Oral immunization with poly-(D,L-lactide-co-glycolide) and poly-(L-lactic acid) microspheres containing pneumotropic bacterial antigens*. International Archives of Allergy & Immunology, 1997. 113(4): p. 424–31.
7. Anderson, P. M. and M. A. Sorenson, *Effects of route and formulation on clinical pharmacokinetics of interleukin-2*. Clin Pharmacokinet, 1994. 27(1): p. 19–31.
8. Handelsman, D. J., R. P. Jansen, L. M. Boylan, J. A. Spaliviero, and J. R. Turtle, *Pharmacokinetics of gonadotropin-releasing hormone: comparison of subcutaneous and intravenous routes*. J Clin Endocrinol Metab, 1984. 59(4): p. 739–46.
9. Harris, D. and J. R. Robinson, *Drug delivery via the mucous membranes of the oral cavity*. J Pharm Sci, 1992. 81(1): p. 1–10.
10. Murrell, W., *Nitro-glycerin as a remedy for angina pectoris*. Lancet, 1879. 151: p. 225–227.
11. Ulmer, J. B., J. J. Donnelly, S. E. Parker, G. H. Rhodes, P. L. Feigner, V. J. Dwarki, S. H. Gromkowski, R. R. Deck, C. M. DeWitt, A. Friedman, L. A. Hawe, K. R. Leander, D. Martinez, H. C. Perry, J. W. Shiver, D. L. Montgomery, and M. A. Liu, *Heterologous protection against influenza by injection of DNA encoding a viral protein*. Science, 1993. 259: p. 1745–1749.
12. Xu, D. and F. Liew, *Protection against leishmaniasis by injection of DNA encoding a major surface glycoprotein, gp63 of L. major*. Immunology, 1995. 84: p. 173–176.
13. Wang, B., A. P. Godillot, M. P. Madaio, D. B. Weiner, and W. V. Williams, *Vaccination against pathogenic cells by DNA inoculation*. Current Topics in Microbiology and Immunology, 1998. 226: p. 21–35.
14. Kim, J. J., N. N. Trivedi, L. K. Nottingham, L. Morrison, A. Tsai, Y. Hu, S. Mahalingam, K. Dang, L. Ahn, N. K. Doyle, D. M. Wilson, M. A. Chattergoon, A. A. Chalian, J. D. Boyer, M. G. Agadjanyan, and D. B. Weiner, *Modulation of amplitude and direction of in vivo immune responses by co-administration of cytokine gene expression cassettes with DNA immunogens*. European Journal of Immunology, 1998. 28(3): p. 1089–1103.
15. Chow, Y. H., B. L. Chiang, Y. L. Lee, W. K. Chi, W. C. Lin, Y. T. Chen, and M. H. Tao, *Development of Th1 and*

15. Th2 populations and the nature of immune responses to hepatitis B virus DNA vaccines can be modulated by codelivery of various cytokine genes. Journal of Immunology, 1998. 160(3): p. 1320–9.
16. Irvine, K. R., J. B. Rao, S. A. Rosenberg, and N. P. Restifo, Cytokine enhancement of DNA immunization leads to effective treatment of established pulmonary metastases. Journal of Immunology, 1996. 156(1): p. 238–45.
17. Sjolander, A., T. M. Baldwin, J. M. Curtis, and E. Handman, Induction of a Th1 immune response and simultaneous lack of activation of a Th2 response are required for generation of immunity to leishmaniasis. Journal of Immunology, 1998. 160(8): p. 3949–3957.
18. Gabaglia, C. R., B. Pedersen, M. Hitt, N. Burdin, E. E. Sercarz, F. L. Graham, J. Gauldie, and T. A. Braciak, A single intramuscular injection with an adenovirus-expressing IL-12 protects BALB/c mice against Leishmania major infection, while treatment with an IL-4-expressing vector increases disease susceptibility in B10.D2 mice. Journal of Immunology, 1999. 162(2): p. 753–60.
19. Nomura, T., K. Yasuda, T. Yamada, S. Okamoto, R. I. Mahato, Y. Watanabe, Y. Takakura, and M. Hashida, Gene expression and antitumor effects following direct interferon (IFN)-gamma gene transfer with naked plasmid DNA and DC-chol liposome complexes in mice. Gene Therapy, 1999. 6(1): p. 121–9.
20. Jones, D. H., S. Corris, S. McDonald, J. C. Clegg, and G. H. Farrar, Poly(DL-lactide-co-glycolide)-encapsulated plasmid DNA elicits systemic and mucosal antibody responses to encoded protein after oral administration. Vaccine, 1997. 15(8): p. 814–7.
21. Wang, D., D. R. Robinson, G. S. Kwon, and J. Samuel, Encapsulation of plasmid DNA in biodegradable poly(D, L-lactic-co-glycolic acid) microspheres as a novel approach for immunogene delivery. Journal of Controlled Release, 1999. 57(1): p. 9–18.
22. Capan, Y., B. H. Woo, S. Gebrekidan, S. Ahmed, and P. P. DeLuca, Preparation and characterization of poly(D, L-lactide-co-glycolide) microspheres for controlled release of poly(L-lysine) complexed plasmid DNA. Pharmaceutical Research, 1999. 16(4): p. 509–13.
23. Walter, E., K. Moelling, J. Pavlovic, and H. P. Merkle, Microencapsulation of DNA using poly(DL-lactide-co-glycolide): stability issues and release characteristics. Journal of Controlled Release, 1999. 61(3): p. 361–74.
24. Ando, S., D. Putnam, D. W. Pack, and R. Langer, PLGA microspheres containing plasmid DNA: preservation of supercoiled DNA via cryopreparation and carbohydrate stabilization. Journal of Pharmaceutical Sciences, 1999. 88(1): p. 126–30.
25. Singh, M., M. Briones, G. Ott, and D. O'Hagan, Cationic microparticles: A potent delivery system for DNA vaccines. Proceedings of the National Academy of Sciences, USA, 2000. 97(2): p. 811–816.
26. Capan, Y., B. H. Woo, S. Gebrekidan, S. Ahmed, and P. P. DeLuca, Influence of formulation parameters on the characteristics of poly(D,L-lactide-co-glycolide) microspheres containing poly(L-lysine) complexed plasmid DNA. J Controlled Release, 1999. 60(2-3): p. 279–86.
27. Hedley, M. L., J. Curley, and R. Urban, Microspheres containing plasmid-encoded antigens elicit cytotoxic T-cell responses. Nature Medicine, 1998. 4(3): p. 365–8.
28. Leong, K. H., A. J. Ramsay, D. B. Boyle, and I. A. Ramshaw, Selective induction of immune responses by cytokines coexpressed in recombinant fowlpox virus. Journal of Virology, 1994. 68(12): p. 8125–30.
29. Kim, J. J., K. A. Simbiri, J. I. Sin, K. Dang, J. Oh, T. Dentchev, D. Lee, L. K. Nottingham, A. A. Chalian, D. McCallus, R. Ciccarelli, M. G. Agadjanyan, and D. B. Weiner, Cytokine molecular adjuvants modulate immune responses induced by DNA vaccine constructs for HIV-1 and SIV. Journal of Interferon and Cytokine Research, 1999. 19(1): p. 77–84.
30. Mao, H.-Q., W. Dang, I. Shipanova-Kadiyala, Z. Zhao, D. Cline, and K. W. Leong. Design of new biodegradable polymers based on chain-extension of oligomeric lactides by phosphates. in Proceedings of the Topical Conference on Biomaterials, Carriers for Drug Delivery, and Scaffolds for Tissue Engineering. 1997. Los Angeles, Calif.: American Institute of Chemical Engineers.
31. Mao, H.-Q., Z. Zhao, W. Dang, I. Shipanova-Kadiyala, and K. W. Leong, Biodegradable Poly(phosphoester)s, in The Encyclopedia of Controlled Drug Delivery, E. Mathiowitz, Editor. 1999, John Wiley & Sons, Inc.: New York.
32. Haller, M. F., H.-Q. Mao, S.-Q. Liu, Z. Zhao, and K. W. Leong, Modulating antibody responses with co-delivery of DNA and cytokines from biodegradable poly (phosphoester) microspheres. Pharmaceutical Research, (Submitted).
33. Eldridge, J. H., C. J. Hammond, J. A. Meulbroek, J. K. Staas, R. M. Gilley, and T. R. Tice, Controlled vaccine release in the gut-associated lymphoid tissues. Journal of Controlled Release, 1990. 2: p. 205–214.,
34. Desai, M. P., V. Labhasetwar, E. Walter, R. J. Levy, and G. L. Amidon, The mechanism of uptake of biodegradable microparticles in Caco-2 cells is size dependent. Pharm Res, 1997. 14(11): p. 1568–73.
35. Tabata, Y. and Y. Ikada, Phagoctyosis of polymer microspheres by macrophages. Advances in Polymer Science, 1990. 94: p. 167–141.
36. Nellore, R. V., P. G. Pande, D. Young, and H. R. Bhagat, Evaluation of biodegradable microspheres as vaccine adjuvant for hepatitis B surface antigen. Journal of Parenteral Science & Technology, 1992. 46(5): p. 176–80.

What is claimed is:

1. A method for delivering a bioactive agent to a mammal's lymph node comprising the steps of:
providing a microparticle or nanoparticle, which comprises at least one biocompatible polymer and a bioactive agent;
instilling an effective amount of said microparticle or nanoparticle into a mammal's bladder such that at least a portion of the instilled microparticles or nanoparticles are localized to a lymph nodes;
wherein the bioactive agent is released from the instilled microparticles or nanoparticles into the lymph node; and
wherein the bioactive agent is selected from small molecule drugs, imaging agents, radioactive therapeutics, dyes, proteins, DNA, RNA and combinations thereof, and wherein the biocompatible polymer is a homopolymer or copolymer comprising one or more monomer repeat units selected from lactic acid, glycolic acid, lactide, lactone, poly(ethylene oxide), and poly (propylene oxide).

2. The method of claim 1, wherein the bioactive agent or a biologically active substance generated from the bioactive agent released from the microparticle into the lymph node is distributed systemically.

3. The method of claim 1, wherein the bioactive agent is selected from the group consisting of DNA, cytokines, immunoadjuvants, cancer therapeutic agents, proteins, and combinations thereof.

4. The method of claim 1, wherein the bioactive agent modulates the immune response of the mammal.

5. The method of claim 4, wherein the bioactive agent is a protein or DNA.

6. The method of claim 5, wherein the bioactive agent is DNA.

7. The method of claim 6, wherein the DNA comprises DNA encoding an antigen, DNA encoding a cytokine or a combination of DNA encoding an antigen and DNA encoding a cytokine.

8. The method of claim 7, wherein the cytokine is selected from an interleukin or interferon, which can shift a mammal's immune response toward either a $T_H1$ or $T_H2$ response.

9. The method of claim 8, wherein the cytokine is selected from interleukin-12, interleukin-10, interleukin-5, interleukin-4, granulocyte-monocyte colony-stimulating factor or interferon-gamma.

10. The method of claim 1, wherein the biocompatible polymer is biodegradable.

11. The method of claim 1, wherein the at least one biocompatible polymer of the nanoparticle is a poly(phoshoester)-poly(D,L-lactide-co-ethylphosphate) copolymer.

12. The method of claim 1, wherein the at least one biocompatible polymer of the microparticle is a polymer comprising repeat units according to Formula I:

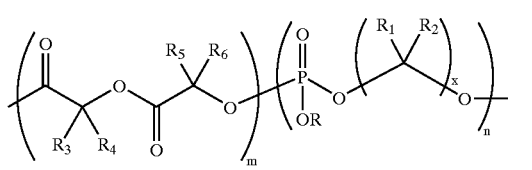

wherein

R is hydrogen, optionally substituted alkyl, optionally substituted $C_{2-12}$-alkenyl, optionally substituted heteroalkyl, optionally substituted $C_{2-12}$-alkynyl, or optionally substituted $C_{5-8}$-cycloalkyl;

$R_1$ and $R_2$ are each independently chosen from the group consisting of H, optionally substituted alkyl, optionally substituted $C_{2-12}$-alkenyl, optionally substituted heteroalkyl, optionally substituted $C_{2-12}$-alkynyl, and optionally substituted alkoxy;

$R_3$ and $R_5$ are hydrogen:

$R_4$ and $R_6$ are independently selected from hydrogen and methyl:

x is 2, 3, or 4;

n and m are non-negative integers;

n+m is about 5 to about 2000; and m:n is between about 1:100 to about 100:1.

13. The method of claim 1, wherein the instilled nanoparticles have an average particle size, measured by average diameter, of between about 250 nanometers and about 5 microns.

14. The method of claim 1, wherein the instilled nanoparticles have an average particle size, measured by average diameter, of between about 500 nanometers and about 3 microns.

15. The method of claim 1, wherein the instilled nanoparticles have an average particle size, measured by average diameter, of between about 600 nanometers and about 2 microns.

16. The method of claim 1, wherein the instilled nanoparticles comprise at least about 0.1% by weight of the bioactive agent.

17. The method of claim 1, wherein the instilled nanoparticles comprise at least about 0.25% by weight of the bioactive agent.

18. The method of claim 1, wherein the instilled nanoparticles comprise at least about 0.5% by weight of the bioactive agent.

19. The method of claim 1, wherein the instilled nanoparticles comprise at least about 1% by weight of the bioactive agent.

20. The method of claim 1, wherein the instilled nanoparticles comprise at least about 2% by weight of the bioactive agent.

21. The method of claim 1, wherein at least 50% of the bioactive agent is delivered to the lymph node.

22. The method of claim 1, wherein at least 75% of the bioactive agent is delivered to the lymph node.

23. The method of claim 1, wherein at least 90% of the bioactive agent is delivered to the lymph node.

24. A method for modulating an immune response in a mammal comprising the steps of:

instilling to the bladder of a mammal an effective amount of a microparticle comprising a biocompatible polymer and one or more bioactive agents capable of modulating an immune response in the mammal thereby transporting the microparticles to a lymph node and releasing the bioactive agent to modulate the immune response, wherein the bioactive agent is selected from small molecule drugs, imaging agents, radioactive therapeutics, dyes, proteins, DNA, RNA and combinations thereof, and wherein the biocompatible polymer is a homopolymer or copolymer comprising one or more monomer repeat units selected from lactic acid, glycolic acid, lactide, lactone, poly(ethylene oxide), and poly(propylene oxide).

25. The method of claim 24, wherein modulation of the immune response increases $T_H1$ immune response.

26. The method of claim 24, wherein modulation of the immune response increases $T_H2$ immune response.

27. A method for systemic delivery of a bioactive agent to a mammal in need of said systemic delivery, the method comprising the steps of:

providing a microparticle or nanoparticle, which comprises at least one biocompatible polymer and a bioactive agent;

instilling an effective amount of said microparticle or nanoparticle into said mammal's bladder under conditions conductive to the transport of said microparticle or nanoparticle across the epithelial layer of the bladder;

wherein the bioactive agent is released systemically from the instilled microparticle or nanoparticle; and wherein the bioactive agent is selected from small molecule drugs, imaging agents, radioactive therapeutics, dyes, proteins, DNA, RNA and combinations thereof, and wherein the biocompatible polymer is a homopolymer or copolymer comprising one or more monomer repeat units selected from lactic acid, glycolic acid, lactide, lactone, poly(ethylene oxide), and poly(propylene oxide).

28. The method of claim 27, wherein the instilled nanoparticles are transported from the bladder, through the mammal's lymphatic vessels, to at least one of the mammal's lymph nodes.

29. The method of claim 28, wherein at least 25% of the nanoparticles instilled in the mammal's bladder are localized to the lymph nodes.

30. The method of claim 28, wherein at least 50% of the nanoparticles instilled in the mammal's bladder are localized to the lymph nodes.

31. The method of claim 28, wherein at least 75% of the nanoparticles instilled in the mammal's bladder are localized to the lymph nodes.

32. The method of claim 28, wherein at least 90% of the nanoparticles instilled in the mammal's bladder are localized to the lymph nodes.

* * * * *